United States Patent
Jeon et al.

(10) Patent No.: US 9,811,886 B2
(45) Date of Patent: Nov. 7, 2017

(54) IMAGE PROCESSING APPARATUS, MEDICAL IMAGING APPARATUS, AND IMAGE PROCESSING METHOD

(71) Applicant: SAMSUNG ELECTRONICS CO., LTD., Suwon-si (KR)

(72) Inventors: Sung W Jeon, Suwon-si (KR); Young Hun Sung, Hwaseong-si (KR); Dong-Goo Kang, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/865,992

(22) Filed: Sep. 25, 2015

(65) Prior Publication Data

US 2016/0209995 A1 Jul. 21, 2016

(30) Foreign Application Priority Data

Jan. 19, 2015 (KR) .................. 10-2015-0008848

(51) Int. Cl.
*G06K 9/00* (2006.01)
*G06T 5/00* (2006.01)
*G06F 19/00* (2011.01)

(52) U.S. Cl.
CPC .......... *G06T 5/003* (2013.01); *G06F 19/3406* (2013.01); *G06T 2207/10072* (2013.01); *G06T 2207/10116* (2013.01); *G06T 2207/20081* (2013.01); *G06T 2207/20092* (2013.01); *G06T 2207/30004* (2013.01)

(58) Field of Classification Search
None
See application file for complete search history.

(56) References Cited

U.S. PATENT DOCUMENTS

| | | | | |
|---|---|---|---|---|
| 5,857,030 A * | 1/1999 | Gaborski | ................ | G06K 9/62 378/37 |
| 8,379,130 B2 * | 2/2013 | Forutanpour | ........ | G11B 27/034 348/333.01 |
| 8,774,476 B2 * | 7/2014 | Urushiya | .................. | G06T 5/50 382/128 |
| 9,681,270 B2 * | 6/2017 | Kamlani | ............... | H04W 4/028 |

(Continued)

FOREIGN PATENT DOCUMENTS

JP 2003-284705 A 10/2003
JP 2009-050465 A 3/2009

*Primary Examiner* — Nancy Bitar
(74) *Attorney, Agent, or Firm* — Sughrue Mion, PLLC

(57) ABSTRACT

Disclosed herein are an image processing apparatus, a medical imaging apparatus, and an image processing method, which may intuitively and easily set an image processing parameter used to process a medical image to a user-preferred optimal value. The image processing apparatus includes a display unit configured to display a plurality of sample images to which at least one image processing parameter has been variably applied; an input unit configured to receive a selection of one from among the displayed plurality of sample images from a user; and an image processing unit configured to generate a plurality of new sample images to which the at least one image processing parameter has been variably applied based on an image processing parameter to be applied to the selected sample image when the user is not satisfied with the selected sample image.

27 Claims, 28 Drawing Sheets

(56) References Cited

U.S. PATENT DOCUMENTS

| | | | | |
|---|---|---|---|---|
| 2004/0264756 | A1* | 12/2004 | Spahn | A61B 6/00 382/132 |
| 2007/0140542 | A1 | 6/2007 | Spahn | |
| 2008/0262354 | A1* | 10/2008 | Yoshida | A61B 8/469 600/443 |
| 2009/0285464 | A1* | 11/2009 | Urushiya | G06T 5/50 382/131 |
| 2009/0303252 | A1* | 12/2009 | Hyun | A61B 6/032 345/643 |
| 2010/0322489 | A1* | 12/2010 | Tizhoosh | G06K 9/6253 382/128 |
| 2013/0182923 | A1* | 7/2013 | Urushiya | G06T 5/50 382/128 |
| 2013/0182926 | A1* | 7/2013 | Lee | G06K 9/00671 382/131 |

* cited by examiner

IMAGE PROCESSING APPARATUS, MEDICAL IMAGING APPARATUS, AND IMAGE PROCESSING METHOD

CROSS-REFERENCE TO RELATED APPLICATION

This application claims priority from Korean Patent Application No. 10-2015-0008848, filed on Jan. 19, 2015 in the Korean Intellectual Property Office, the disclosure of which is incorporated herein by reference in its entirety.

BACKGROUND

1. Field

Exemplary embodiments relate to an image processing apparatus, a medical imaging apparatus, and an image processing method, in which a user may set a parameter which is applicable for processing a medical image.

2. Description of the Related Art

A medical imaging apparatus is an apparatus for imaging an inside of a target object for the purpose of facilitating a diagnostic or surgical procedure. Various examples of the medical imaging apparatus include a medical ultrasound imaging apparatus, a typical radiography apparatus, a magnetic resonance imaging (MRI) apparatus, a mammography apparatus, a positron emission tomography (PET) apparatus, a computed tomography (CT) apparatus, a single photon emission computed tomography (SPECT) apparatus, an optical coherence tomography (OCT) apparatus, and the like.

A medical image acquired by a medical imaging apparatus is processed and then displayed on a display device. A user, such as a doctor and/or a radiologic technologist, may perform a diagnostic or surgical procedure or control photographing to obtain a medical image.

SUMMARY

Therefore, it is an aspect of one or more exemplary embodiments to provide an image processing apparatus, a medical imaging apparatus, and an image processing method, which may intuitively and easily set an image processing parameter which is usable for processing a medical image to a user-preferred optimal value.

Additional aspects of the exemplary embodiments will be set forth in part in the description which follows and, in part, will be apparent from the description, or may be learned by practice of the exemplary embodiments.

In accordance with one aspect of one or more exemplary embodiments, an image processing apparatus includes a display configured to display a first plurality of sample images to which at least one image processing parameter from among a plurality of image processing parameters has been variably applied; an input device configured to receive, from a user, a selection of one sample image from among the displayed first plurality of sample images; and an image processor configured to generate a second plurality of new sample images to which the at least one image processing parameter has been variably applied based on an image processing parameter applied to the selected sample image when the user is not satisfied with the selected sample image.

The image processing apparatus may further include a parameter controller configured to control the plurality of image processing parameters applied by the image processor.

The parameter controller may be further configured to optimize the at least one image processing parameter applied to the selected sample image based on machine learning.

The image processor may be further configured to repeatedly perform the generation of the second plurality of new sample images until the user is satisfied with the selected sample image, and the display may be further configured to repeatedly perform a display of the generated second plurality of sample images.

The image processing apparatus may further include a storage configured to store preference data which relates to respective preferences of each of a plurality of users for the plurality of image processing parameters in which the preference data includes a respective setting history of the plurality of image processing parameters for each of the plurality of users.

The parameter controller may be further configured to set the at least one image processing parameter based on a sample image finally selected by the user.

In accordance with another aspect, an image processing apparatus includes: a display configured to display a first plurality of sample images to which a first image processing parameter from among a plurality of image processing parameters has been variably applied to a second plurality of sample images to which an nth image processing parameter from among the plurality of image processing parameters has been variably applied, where n is an integer that is greater than or equal to two; an input device configured to receive, from a user, a selection of one sample image from among the displayed first plurality of sample images; and a parameter controller configured to set the first image processing parameter based on the nth image processing parameter applied to the selected sample image.

The parameter controller may be further configured to store the plurality of image processing parameters that are applied to the selected sample image.

The parameter controller may be further configured to optimize the plurality of image processing parameters that are applied to the selected sample image based on machine learning and to store the optimized plurality of image processing parameters.

In accordance with still another aspect, an image processing apparatus includes: a display configured to display a first plurality of sample images to which at least a first image processing parameter from among a plurality of image processing parameters has been variably applied; an input device configured to receive, from a user, a selection of one sample image from among the displayed first plurality of sample images; and a parameter controller configured to set the at least first image processing parameter based on a second image processing parameter from among the plurality of image processing parameters that is applied to the selected sample image, and when the at least first image processing parameter is changed, to optimize the changed image processing parameter based on machine learning.

The parameter controller may be further configured to perform a setting of the at least first image processing parameter upon an initial execution performed by the image processing apparatus or periodically.

The parameter controller may be further configured to include the changed image processing parameter in learning data which is used for the application of the machine learning.

In accordance with even another aspect, a medical imaging apparatus includes: a scanner configured to scan a target object in order to acquire a medical image; and an image processing apparatus configured to set at least a first image processing parameter from among a plurality of image processing parameters to be applied to the medical image, in which the image processing apparatus includes a display configured to display a first plurality of sample images to which the at least first image processing parameter has been variably applied; an input device configured to receive, from a user, a selection of one sample image from among the displayed first plurality of sample images; and an image processor configured to generate a second plurality of new sample images for which the at least first image processing parameter has been variably applied based on an image processing parameter applied to the selected sample image when the user is not satisfied with the selected sample image.

In accordance with yet another aspect, an image processing method includes displaying a first plurality of sample images to which at least a first image processing parameter from among a plurality of image processing parameters has been variably applied; receiving, from a user, a selection of one sample image from among the displayed first plurality of sample images; and generating a second plurality of new sample images to which the at least first image processing parameter has been variably applied based on an image processing parameter applied to the selected sample image when the user is not satisfied with the selected sample image.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Hereinafter, a medical imaging apparatus, an image processing apparatus, and an image processing method according to one or more exemplary embodiments will be described in detail with reference to the accompanying drawings.

Figure 1:
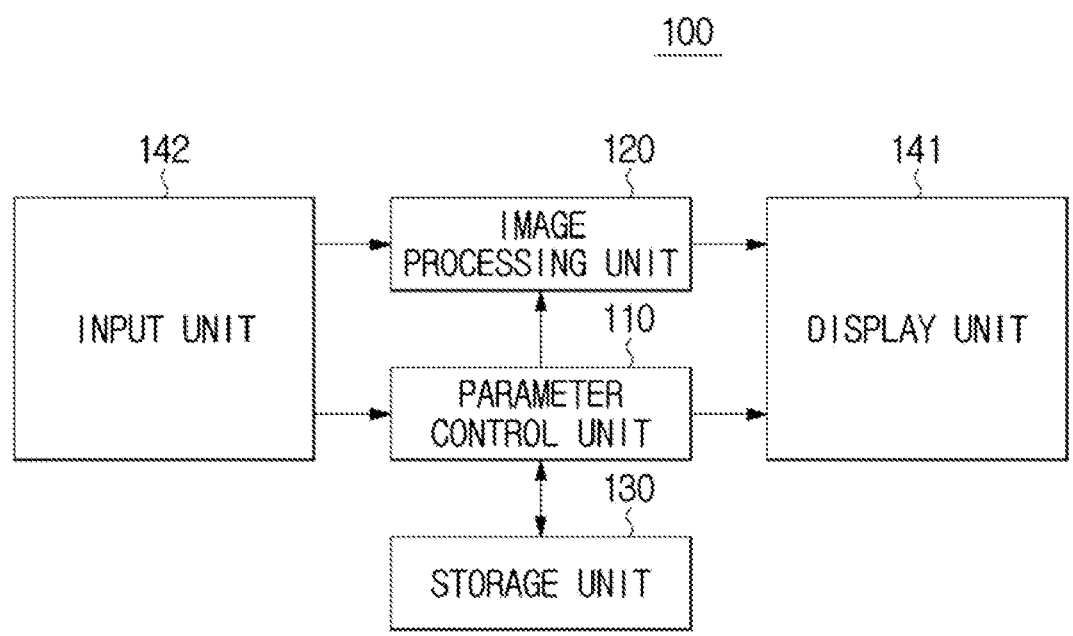
FIG. 1 is a control block diagram illustrating an image processing apparatus, according to an exemplary embodiment.

FIG. 1 is a control block diagram illustrating an image processing apparatus, according to an exemplary embodiment.

Referring to FIG. 1, an image processing apparatus 100 according to an exemplary embodiment includes a parameter control unit (also referred to herein as a "parameter controller") 110 configured to control at least one image processing parameter to be applied with respect to a medical image, an image processing unit (also referred to herein as an "image processor") 120 configured to perform image processing with respect to the medical image, a storage unit (also referred to herein as a "storage device" and/or as a "storage") 130 configured to store a user's preference for the image processing parameter, a display unit (also referred to herein as a "display device" and/or as a "display") 141 configured to display a plurality of sample images for which image processing parameters have been variably applied, and an input unit (also referred to herein as an "input device") 142 configured to receive a selection of an image processing parameter from the user.

The image processing unit 120 may receive a medical image, and the image processing unit 120 is configured to perform image processing operations with respect to the received medical image. However, the medical image received by the image processing unit 120 does not necessarily need to have the form of an image that is recognizable by a user, but may include a set of data that may become the recognizable image. For example, scan data which relates to a target object may be received by the image processing unit 120 and processed by the image processing unit 120, thus completely converting the scan data into the form of a recognizable image.

The image processing operations performed by the image processing unit 120 may include pre-processing operations and post-processing operations. The pre-processing operations may be performed by converting measurement data acquired by scanning a target object into an intended image, and the post-processing operations may be performed for image enhancement or performed to display an image in a user's desired viewpoint. Detailed processes performed during the pre-processing operations and the post-processing operations may vary depending on a type of the medical image that is subject to the image processing. For example, the pre-processing operations with respect to a computed tomography image may be intended to convert profile values of measurement data obtained via projections into a desired form, and may be performed by comparison with data stored in a calibration file. The post-processing operations may be intended to adjust a parameter such as any of contrast, brightness, noise, sharpness, a structure, latitude, and the like, and may be performed by adjusting the parameter to a user's desired value.

The parameter control unit 110 is configured to control a series of processes for setting an image processing parameter as a user's desired value. In particular, the image processing parameter may include a parameter to be applied for the post-processing operations, for example, any of a parameter for adjusting contrast, a parameter for adjusting brightness, a parameter for adjusting noise, a parameter for adjusting sharpness, and the like. The parameter may be referred to as an image look parameter.

The parameter control unit 110 may generate a plurality of sample images by controlling the image processing unit 120 to perform different image processing operations on the same image, display the generated plurality of sample images via the display unit 141, and perform an operation of setting an image processing parameter or an operation of performing a next image processing operation according to a user's selection. More detailed operations of the parameter control unit 110 will be described below.

The parameter control unit 110 and the image processing unit 120 may include a memory having a program stored therein that can execute each operation and a processor configured to execute the program stored in the memory. The parameter control unit 110 and the image processing unit 120 may include respective processors and respective memories and may share a processor and memory. In particular, the memories may be included in the storage unit 130 to be described below, or may be provided separately from the storage unit 130. In addition, a learning module and/or a determination module of the parameter control unit 110 to be described below may be implemented by using separate processors or may share the same processor.

The storage unit 130 may include a storage medium, for example, any of a semiconductor memory such as a random access memory (RAM), a read only memory (ROM), and a flash memory, a magnetic memory such as a magnetic disk, and an optical disc such as a CR-ROM.

The storage unit 130 may include a user preference database (DB) in which a user's preference for an image processing parameter is stored, and the image processing unit 120 may generate a plurality of sample images based on the stored user's preference. The user's preference for the image processing parameter may include data that relates to parameters generally preferred by many users or a combination thereof, or statistical data that relates to the parameters. For example, the user preference DB may stores values of image processing parameters that are selected or set when many users display a medical image, or statistical data that relates to the values.

The storage unit 130 may store preferences of many users, and many users may use the same or different image processing apparatuses 100. Furthermore, the users may include a radiologic technologist, a doctor, or the like who acquires a medical image or provides medical diagnosis or treatment using the medical image, irrespective of the use of the image processing apparatus 100.

The display unit 141 displays the sample images generated by the image processing unit 120 that performs image processing operations. Furthermore, the display unit 141 may display information that relates to photographing conditions for the medical image, information associated with control of the image processing parameters, a screen for leading to a user's selection, and so on.

The display unit 141 may be implemented as at least one of various display devices, such as a liquid crystal display (LCD), a light emission diode (LED), a plasma display panel (PDP), and an organic light emission diode (OLED).

The input unit 142 may be implemented as at least one of various input devices, such as a jog shuttle, a trackball, a button, a mouse, a keyboard, and a touch panel. When the input unit 142 is implemented as a touch panel, the input unit 142 may be combined with the display unit 141 to form a touch screen.

Figure 2:
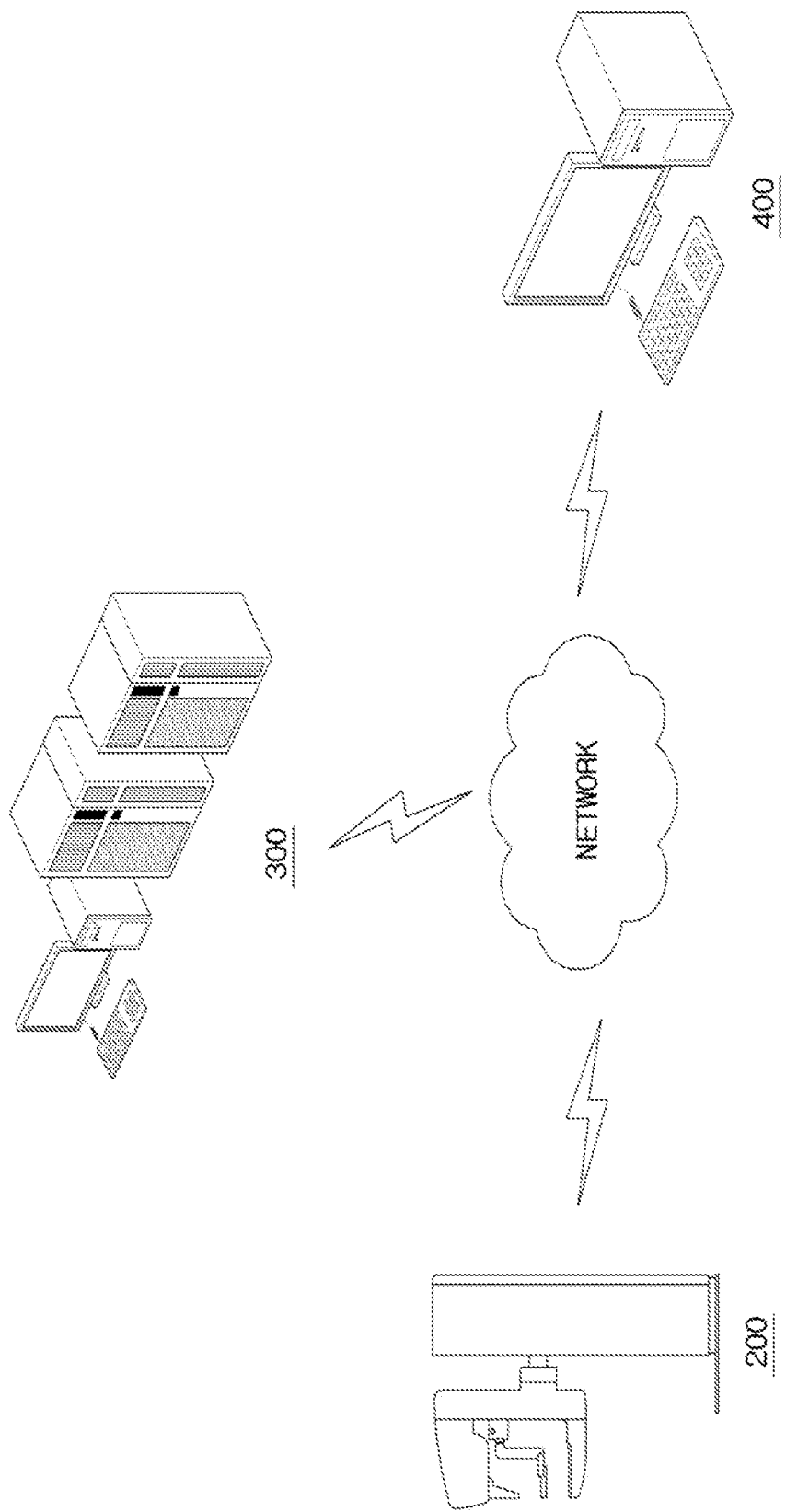
FIG. 2 is a view illustrating apparatuses that may use, as an element, an image processing apparatus, according to an exemplary embodiment.

FIG. 2 is a view illustrating apparatuses that may use, as an element, the image processing apparatus, according to an exemplary embodiment.

Referring to FIG. 2, the image processing apparatus 100 according to an exemplary embodiment may be included in, or implemented as, a medical imaging apparatus 200 that is configured to scan a target object in order to acquire a medical image. Alternatively, the image processing apparatus 100 may be included in, or implemented as, a central server 300 that integrally stores and manages medical images acquired by the medical imaging apparatus 200. In particular, the central server 300 may be a picture archive communication system (PACS). Alternatively, the central server 300 may be included in, or implemented as, a user computer 400 that is provided separately from the medical imaging apparatus 200.

The medical imaging apparatus 200, the central server 300, and the user computer 400 may communicate with each other via a network. Accordingly, the medical image acquired by the medical imaging apparatus 200 may be transmitted to the central server 300 or the user computer 400. For this purpose, the image processing apparatus 100 may include one or more communication modules which are configured for communicating with an external apparatus. For example, the image processing apparatus 100 may include any of a short-range communication module, a wired communication module, and a wireless communication module.

The short-range communication module denotes a module that is configured for performing short-range communication with an apparatus that is positioned within a certain distance. Examples of a short-distance communication technology that may be applied to an embodiment include, but are not limited to, wireless LAN, Wi-Fi, Bluetooth, Zigbee, Wi-Fi Direct (WFD), ultra wideband (UWB), Infrared Data Association (IrDA), Bluetooth Low Energy (BLE), and near field communication (NFC).

The wired communication module denotes a communication module that is configured for performing communication by using an electronic signal or an optical signal. The wired communication technology will include a wired communication technology using any of a pair cable, a coaxial cable, and an optical fiber cable. However, the exemplary embodiments are not limited thereto, and the wired communication technology may include a wired communication technology that is known to one of skill in the art.

The wireless communication module may include an antenna or a wireless communication chip that is configured for transmitting and/or receiving a wireless signal to and/or from at least one of a base station, an external apparatus, and a server in a mobile communication network. For example, the wireless communication module may support Wireless LAN Specification IEEE802.11x of Institute of Electrical and Electronics Engineers (IEEE).

As described above, the image processing apparatus 100 may be included in, or implemented as, at least one of the medical imaging apparatus 200, the central server 300, and the user computer 400. However, for convenience of description, it will be described below that the image processing apparatus 100 is included in the medical imaging apparatus 200.

Figure 3:
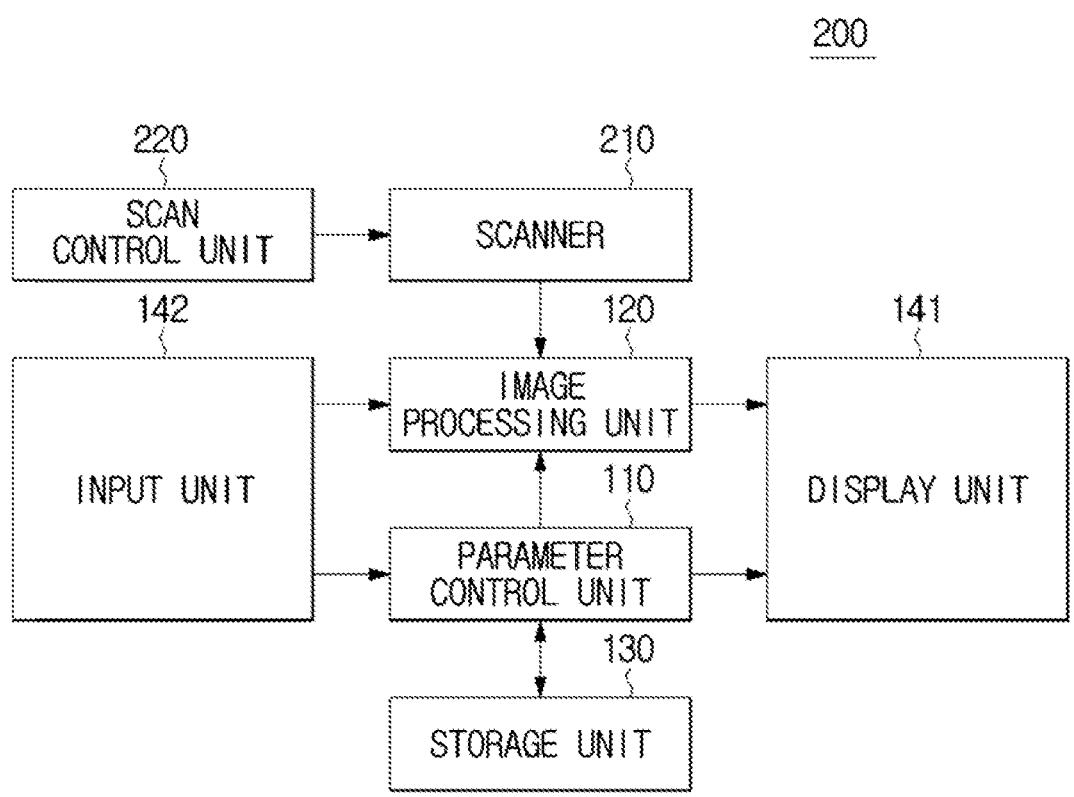
FIG. 3 is a control block diagram illustrating a medical imaging apparatus, according to an exemplary embodiment.

FIG. 3 is a control block diagram illustrating a medical imaging apparatus, according to an exemplary embodiment.

The medical imaging apparatus 200 includes a scanner 210 configured to scan a target object to acquire a medical image, a scan control unit (also referred to herein as a "scan controller") 220 configured to control a scan parameter, and the image processing apparatus 100.

The scanner 210 may deliver the acquired medical image to the image processing apparatus 100 and may have a variable configuration and operation based on the type of the medical image. In addition, the type of a scan parameter the scan control unit 220 is configured to control may vary based on the type of the medical image. The configuration of the scanner 210 and the operation of the scan control unit 220 are described below according to the type of the medical image.

Figure 4:
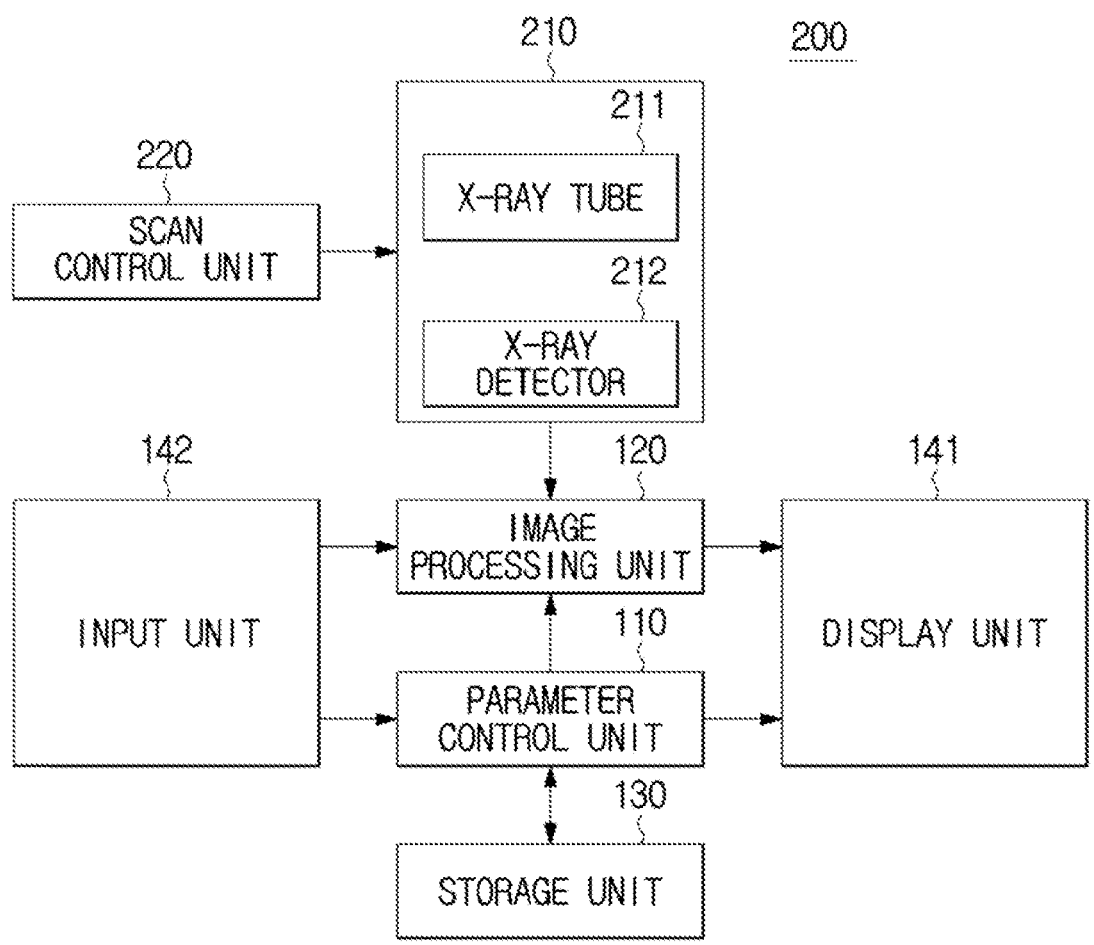
FIG. 4 is a control block diagram illustrating a case in which a medical imaging apparatus acquires an X-ray image.
Figure 5:
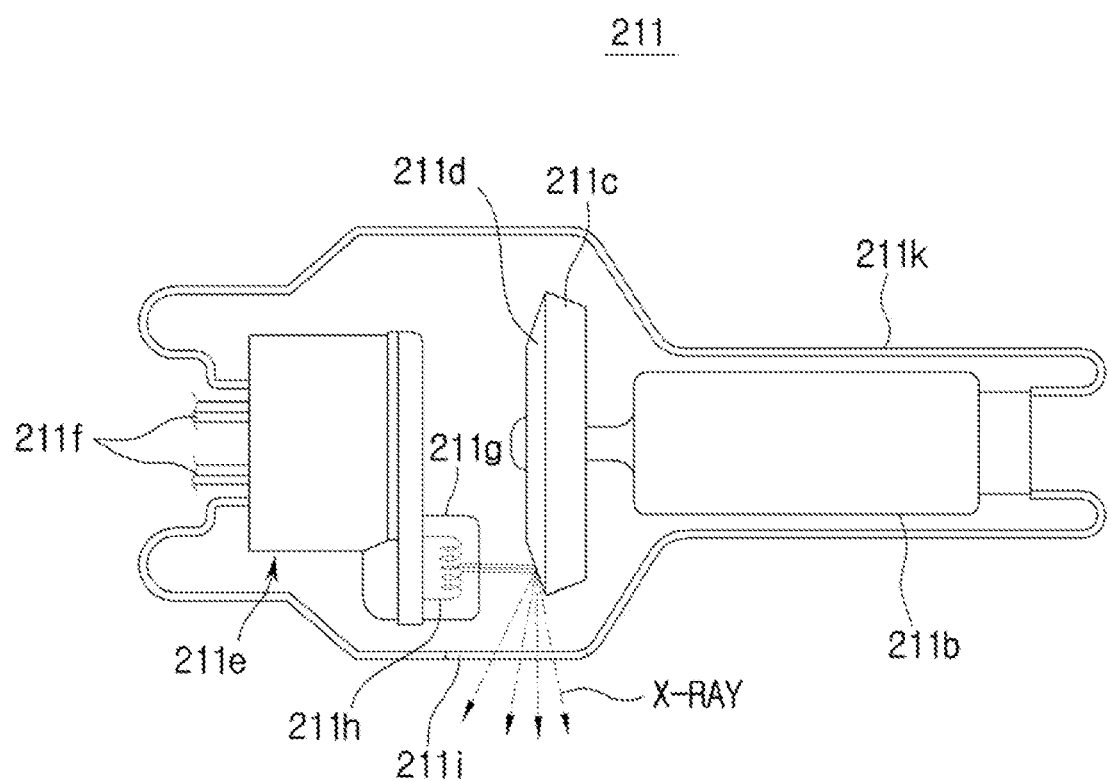
FIG. 5 is a diagram illustrating a configuration of an X-ray tube.
Figure 6:
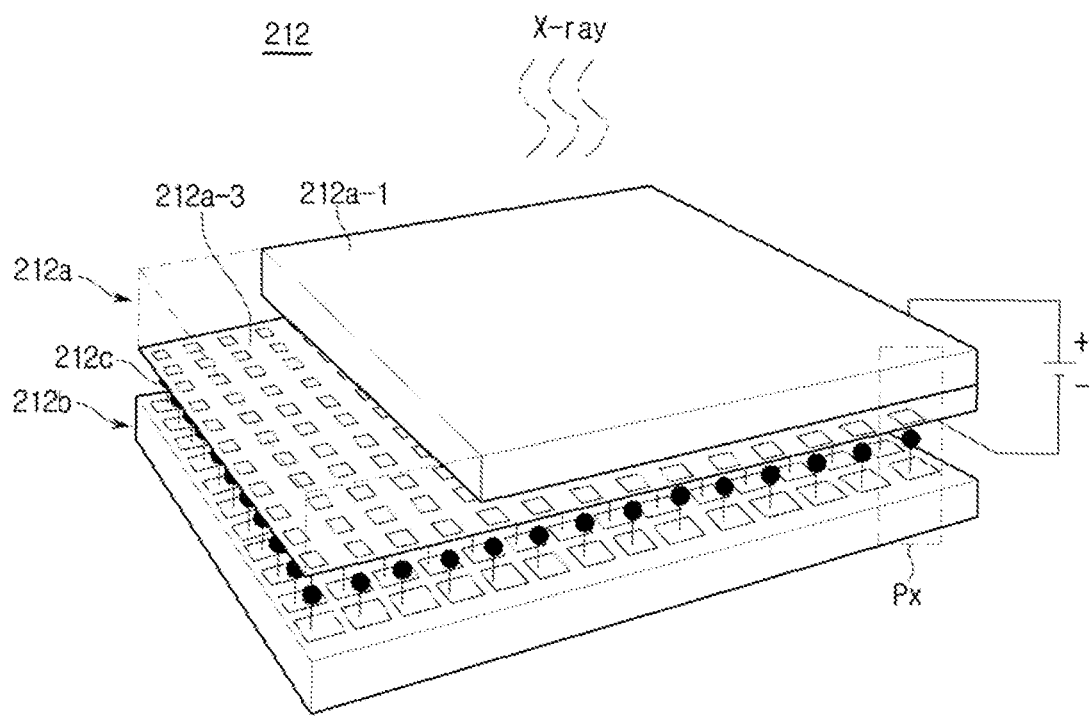
FIG. 6 is a diagram illustrating a configuration of an X-ray detector.

FIG. 4 is a control block diagram illustrating a case in which a medical imaging apparatus acquires an X-ray image, FIG. 5 is a diagram illustrating a configuration of an X-ray tube, and FIG. 6 is a diagram illustrating a configuration of an X-ray detector.

Referring to FIG. 4, when the medical imaging apparatus 200 acquires the X-ray image, the scanner 210 may include an X-ray tube 211 configured to produce and irradiate X-rays and an X-ray detector 212 configured to detect the irradiated X-rays.

Referring to FIG. 5, the X-ray tube 211 may be implemented as a diode vacuum tube which includes an anode 211c and a cathode 211e. The cathode 211e includes a filament 211h and a focusing electrode 211g that is configured to focus electrons, and the focusing electrode 211g is referred to an a focusing cup.

The inside of a glass tube 211k is evacuated to a high vacuum state of about 10 mm Hg, and the filament 211h of the cathode 211e may be heated to a high temperature in order to generate thermal electrons. For example, the filament 211h may be a tungsten filament, and the filament 211h may be heated by applying a current to electrical leads 211f connected to the filament 211h.

The anode 211c may be made of copper, and a target material 211d is applied or disposed on a surface of the anode 111c facing the cathode 211e. The target material 211d may be a high-resistance material, such as, e.g., any of Cr, Fe, Co, Ni, W, and/or Mo. The target material is sloped at a certain angle. As the sloped angle increases, a focal spot size decreases. In addition, the focal spot size may vary based on a tube voltage, a tube current, a size of the filament, a size of the focusing electrode, and/or a distance between the anode and the cathode.

When a high voltage is applied between the cathode 211e and the anode 211c, thermal electrons are accelerated and collide with the target material 211d of the anode 211c, thereby generating X-rays. The generated X-rays are emitted to the outside via a window 211i. The window 211i may be formed of a beryllium (Be) thin film. Also, though not shown in FIG. 5, a filter may be provided on the front or rear side of the window 211i in order to filter a specific energy band of X-rays. In addition, a collimator may be disposed on the front side of the window 211i in order to adjust a field of view (FOV) of the X-rays and reduce scattering of X-rays.

The target material 211d may be rotated by a rotor 211b. When the target material 211d rotates, a heat accumulation rate may increase by ten times per unit area and the focal spot size may be reduced, as compared to when the target material 211d is fixed.

The voltage that is applied between the cathode 211e and the anode 211c of the X-ray tube 211 is called a tube voltage. The magnitude of the tube voltage may be expressed as a crest value (kVp). When the tube voltage increases, a velocity of thermal electrons increases accordingly. Then, an energy (energy of photons) of X-rays that are generated when the thermal electrons collide with the target material 211d also increases.

The current flowing through the X-ray tube 211 is called a tube current, and can be expressed as an average value (mA). When the tube current increases, the number of thermal electrons emitted from the filament 211h increases, and as a result, a dose of X-rays (that is, the number of X-ray photons) that are generated when the thermal electrons collide with the target material 211d increases correspondingly.

In summary, an energy level of X-rays can be controlled by adjusting a tube voltage. Also, a dose or intensities of X-rays can be controlled by multiplication (mAs) of a tube current (mA) and an X-ray exposure time (s).

When the X-rays to be irradiated have a predetermined energy band, the predetermined energy band may be defined by upper and lower limits. The different energy bands may have at least one of upper and lower limits of energy bands which are different from one another.

The upper limit of the predetermined energy band, that is, maximum energy of X-rays to be irradiated, may be adjusted based on the magnitude of a tube voltage, and the lower limit of the predetermined energy band, that is, minimum energy of X-rays to be irradiated, may be adjusted by using a filter. By filtering out a low energy band of X-rays using the filter, an average energy level of X-rays to be irradiated may increase.

When X-rays irradiated by the X-ray tube 211 are incident to the X-ray detector 212 after propagating through a target object, the X-ray detector 212 detects and converts the incident X-rays into electrical signals. The electrical signals correspond to X-ray image signals.

The X-ray detector 212 can be classified according to its material configuration, a method of converting detected X-rays into electrical signals, and/or a method of acquiring electrical signals.

The X-ray detector 212 may be divided into a mono type device or a hybrid type device according to its material configuration.

If the X-ray detector 212 is a mono type device, a part configured for detecting X-rays and generating electrical signals and a part configured for reading and processing the electrical signals may be made of the same semiconductor material, or may be manufactured by one process. In this case, the X-ray detector 212 may be a charge-coupled device (CCD) or a complementary metal-oxide semiconductor (CMOS) which is a light receiving device.

If the X-ray detector 212 is a hybrid type device, a part configured for detecting X-rays and generating electrical signals and a part configured for reading and processing the electrical signals may be made of different materials, or may be manufactured by different processes. For example, there are a case of detecting X-rays by using a photodiode, a CCD, or a light receiving device such as CdZnTe, and reading and processing electrical signals by using a CMOS readout integrated circuit (CMOS ROIC), a case of detecting X-rays by using a strip detector, and reading and processing electrical signals by using a CMOS ROIC, and a case of using an amorphous silicon (a-Si) or an amorphous selenium (a-Se) flat panel system.

The X-ray detector 212 may use a direct conversion mode and/or an indirect conversion mode according to a method of converting X-rays into electrical signals.

In the direct conversion mode, if X-rays are irradiated, electron-hole pairs are temporarily generated in a light receiving device, electrons move to an anode and holes move to a cathode due to an electric field which is applied to both terminals of the light receiving device, and the X-ray detector 212 converts the movement of the electrons and holes into an electrical signal. The light receiving device may be made of any of a-Si, CdZnTe, HgI2, or PbI2.

In the indirect conversion mode, if X-rays irradiated from the X-ray tube 211 react with a scintillator to emit photons having a wavelength within a visible light region, the light receiving device detects and converts the photons into an electrical signal. The light receiving device may be made of amorphous silicon (a-Si), and the scintillator may include any of a gadolinium oxysulfide (GADOX) scintillator of a thin film type, and/or a thallium-doped cesium iodide (CsI (Tl)) of a micro pillar type or a needle type.

The X-ray detector 212 may use a charge integration mode which entails storing charges during a predetermined time period and then acquiring a signal from the stored charges, or a photon counting mode which entails counting the number of photons whenever a signal is generated by single X-ray photons, according to a method of acquiring electrical signals.

As an example, the X-ray detector 212 may have a two-dimensional (2D) array structure having a plurality of pixels Px, as shown in FIG. 6. Referring to FIG. 6, the X-ray detector 212 may include a light receiving device (also referred to herein as a "light receiver") 212a configured to detect X-rays and to generate electrical signals, and a read-out circuit 212b configured to read out the generated electrical signals.

The light receiving device 212a may be made of a single crystal semiconductor material in order to ensure high resolution, high response speed, and a high dynamic area even under conditions of relatively low energy and a relatively small dose of X-rays. The single crystal semiconductor material may include any of Ge, CdTe, CdZnTe, and/or GaAs.

The light receiving device 212a may be in the form of a PIN photodiode. The PIN photodiode is fabricated by bonding a p-type semiconductor substrate 212a-3 of a 2D array structure under an n-type semiconductor substrate 212a-1 with high resistance.

The read-out circuit 212b, which is fabricated according to a CMOS process, is in the form of a 2D array structure and may be coupled with the p-type semiconductor substrate 212a-3 of the light receiving device 212a in units of pixels. A flip-chip bonding (FCB) method of forming bumps 212b by using any of solder (PbSn), indium (In), or the like, reflowing, applying heat, and then compressing may be used.

Meanwhile, the scanner 210 may include both of the X-ray tube 211 and the X-ray detector 212 in a fabrication step. Alternatively, the scanner 210 may include only the X-ray tube 211 in a fabrication step, and a separate X-ray detector 212 may be used together with the scanner 210. In the latter case, the X-ray detector may be implemented in a portable device, and fabricated by the same manufacturer as or a different manufacturer from that of the medical imaging apparatus.

The scan control unit 220 may be configured to control scan parameters related to the X-ray tube 211, for example, any of a tube voltage, a tube current, an exposure time, a filter type, and a type and a rotation speed of a target material. Accordingly, the scan control unit 220 may facilitate a manual control of the scan parameters according to a user's selection, or may perform auto exposure control that automatically controls the scan parameters by using a scout image or a pre-shot image. In addition, the scan control unit 220 may control a signal read-out of the X-ray detector 212.

Figure 7:
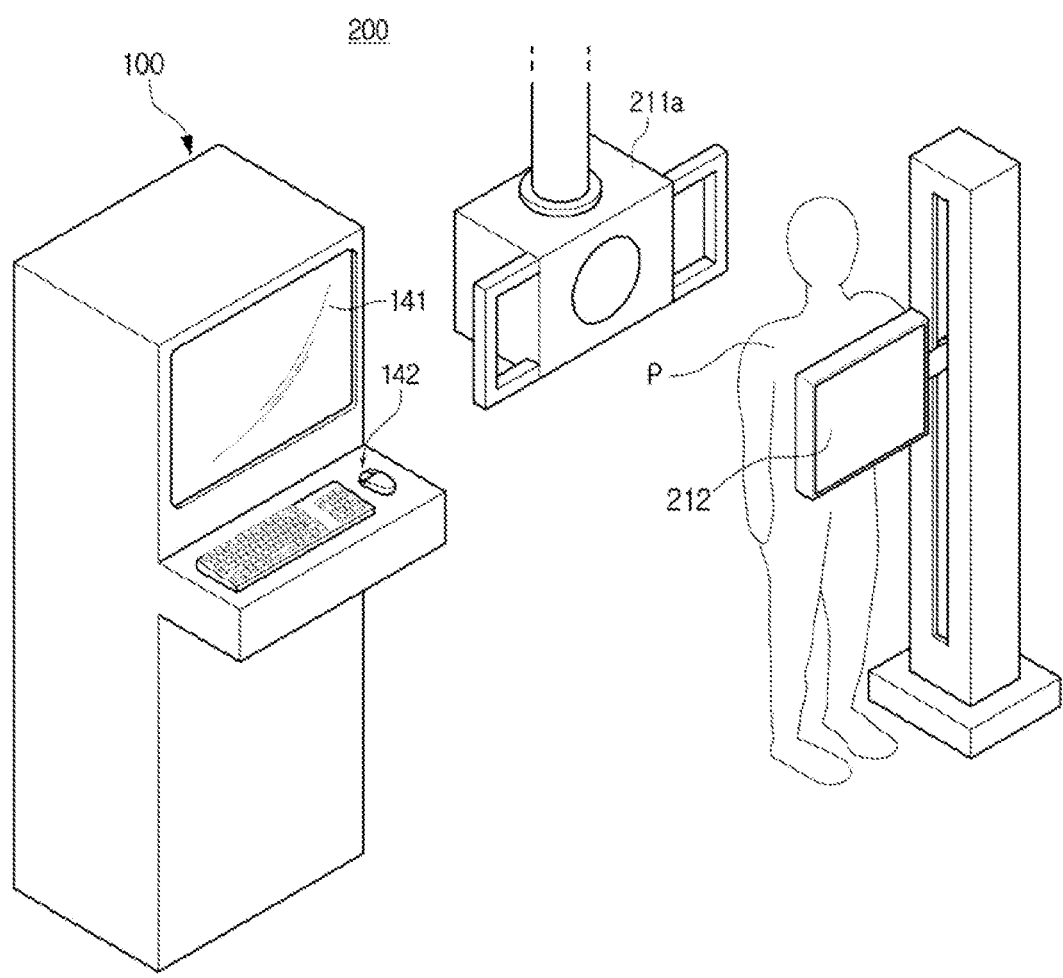
FIG. 7 is an appearance diagram illustrating a case in which a medical imaging apparatus acquires a general radiography image.
Figure 8:
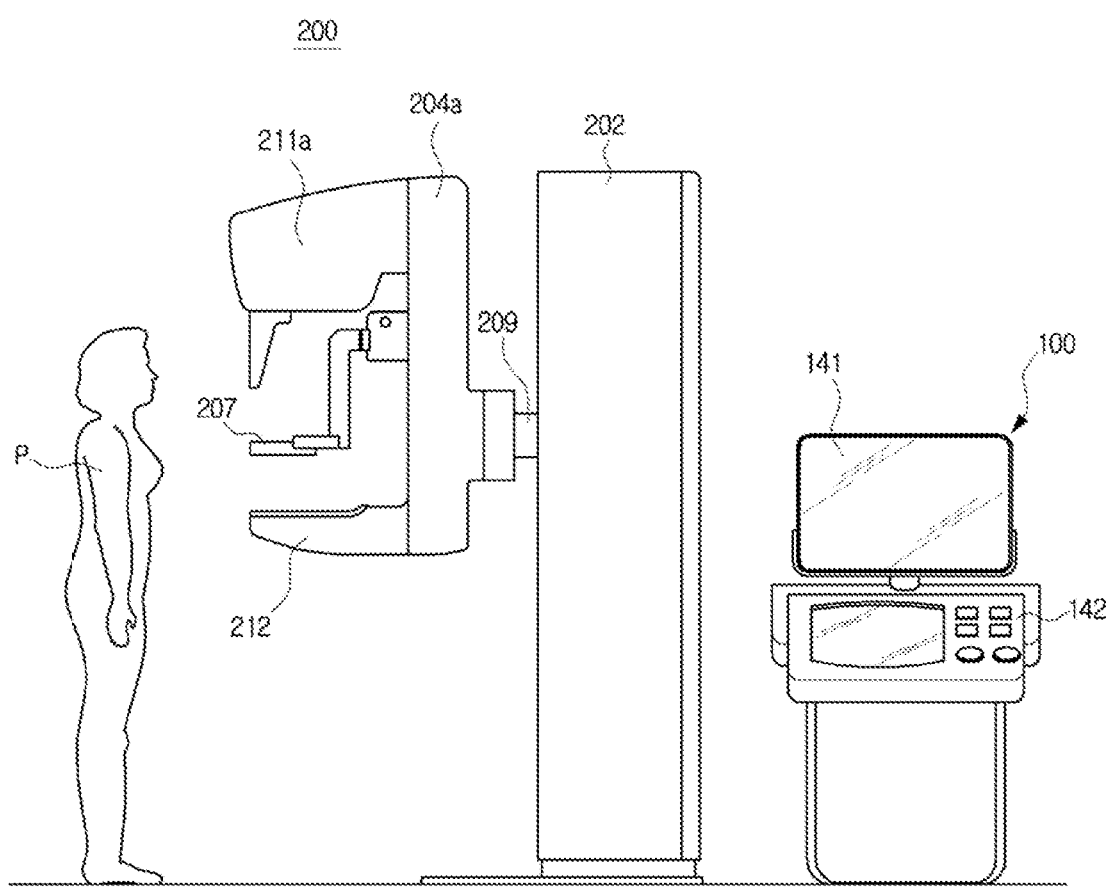
FIG. 8 is an appearance diagram illustrating a case in which a medical imaging apparatus acquires an X-ray image of a breast.
Figure 9:
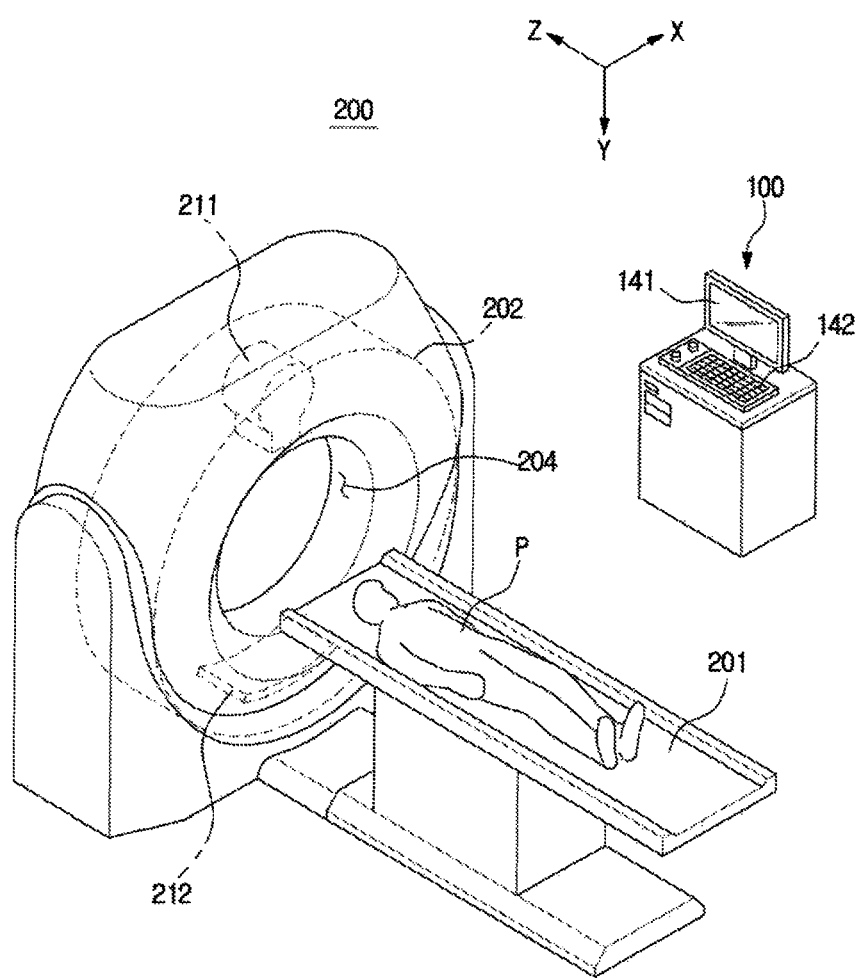
FIG. 9 is an appearance diagram illustrating a case in which a medical imaging apparatus acquires a computed tomography image.

FIG. 7 is an appearance diagram illustrating a case in which a medical imaging apparatus acquires a general radiography image, FIG. 8 is an appearance diagram illustrating a case in which a medical imaging apparatus acquires an X-ray image of a breast, and FIG. 9 is an appearance diagram illustrating a case in which a medical imaging apparatus acquires a computed tomography image.

Even if the inside of the target object is imaged using the same X-rays, different types of images may be generated according to a diagnosis that is based on the X-rays or the purpose of a surgery operation. For example, the medical imaging apparatuses 200 that may acquire images by using general radiography for photographing a still image of a chest, an arm, a leg, and the like, fluoroscopy for photographing a X-ray video such as image angiography, computed tomography for photographing a tomography image or 3D image of a patient, mammography for photographing an X-ray image of a breast, and tomosynthesis for photographing a tomography image or 3D image of a breast have different structures and operations.

As an example, as shown in FIG. 7, when the medical imaging apparatus 200 acquires a general radiography image, the X-ray tube 211 may be built in a tube head 211a connected to a ceiling of a radiation room, and a height of the tube head 211a may be controlled. In addition, when the tube head 211a is implemented in a sealing type, the tube head 211a may move forward, backward, left, and right along a guide rail provided on the ceiling of the radiation room.

A patient P is positioned between the X-ray tube 211 and the X-ray detector 212, and a part to be photographed may include any of a chest, an arm, a leg, etc.

In an example illustrated in FIG. 7, the X-ray detector 212 may be implemented in a stand type. However, the medical imaging apparatus 200 according to an exemplary embodiment is not limited thereto, and the X-ray detector 212 may be inserted into a patient table or implemented as a portable device.

The medical imaging apparatus 200 may include a workstation that provides a user interface, and any of various kinds of memories, microprocessors, and so on built in the workstation may control processing or photographing of images. As an example, the image processing apparatus 100 may be included in the work station, or the image processing apparatus 100 may be implemented as the workstation, as shown in FIG. 7. In this case, a display unit 141 and an input unit 142 may be provided to the workstation. However, this is merely an example, and all elements of the image processing apparatus 100 may not necessarily be included in the workstation. Accordingly, some of the elements of the image processing apparatus 100 are included in the workstation, and others may be included in the tube head 211*a*.

As another example, as shown in FIG. 8, when the medical imaging apparatus 200 performs mammography to acquire a breast image, a breast of the patient P is positioned between the tube head 211*a* and the X-ray detector 212, and a pressure paddle 207 is further included between the tube head 211*a* and the X-ray detector 212 in order to compress the breast. When the pressure paddle 207 compresses the breast, the thickness thereof decreases in a direction in which X-rays are irradiated, thereby helping implement a low dose and enabling materials which are vertically overlapping with respect to each other to be spread laterally.

Even when the medical imaging apparatus 200 performs mammography, the medical imaging apparatus 200 may include a workstation. As described above, the image processing apparatus 100 may be included in a workstation, or as shown in FIG. 8, the image processing apparatus 100 may be implemented as the workstation.

As still another example, as shown in FIG. 9, when the medical imaging apparatus 200 performs computed tomography to acquire a tomography image, the X-ray tube 211 and the X-ray detector 212 are positioned to face each other and are installed in a gantry 202. When a patient table 201 transports the patient P to a bore 204, the gantry 202 scans the patient P while rotating around the bore 204, and thus acquires projection data.

In this case, projection data that relates to the patient P is acquired by the scanner 210, and the projection data is input to the image processing apparatus 100. Likewise, the image processing apparatus 100 may be included in the workstation, or implemented as the workstation as shown in FIG. 9, and the display unit 141 and the input unit 142 may be provided to the workstation.

The image processing unit 120 may reconstruct the projection data in order to generate a sectional plane image, or accumulate a plurality of sectional plane images in order to generate a three-dimensional (3D) volume data.

Figure 10:
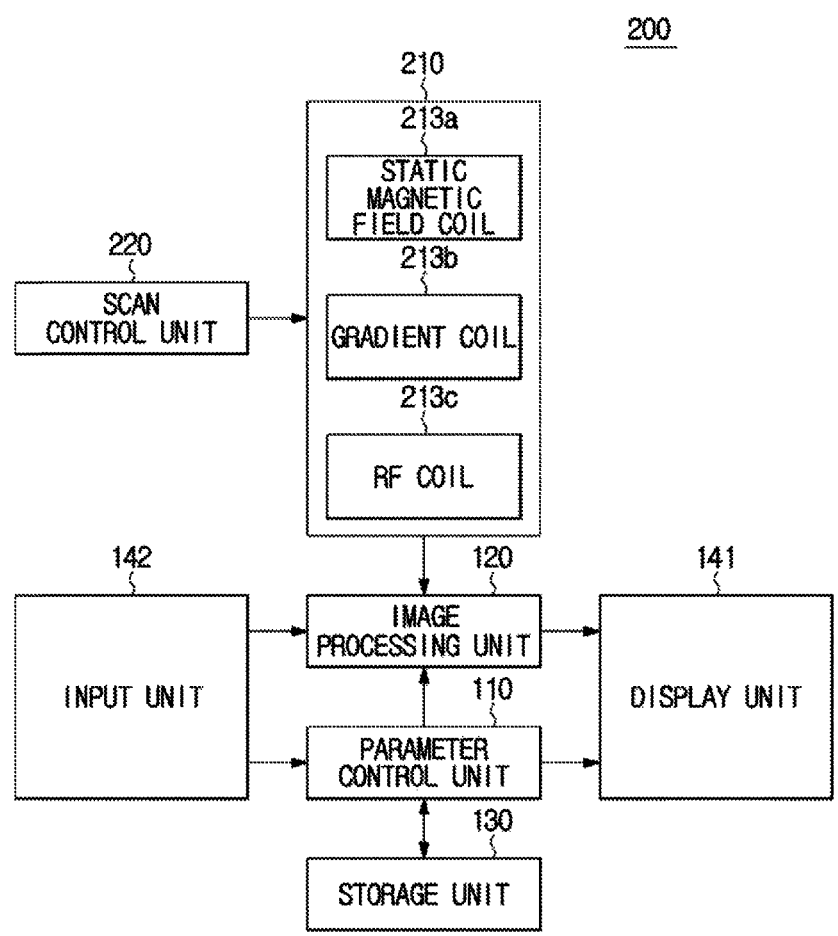
FIG. 10 is a control block diagram illustrating a case in which a medical imaging apparatus acquires a magnetic resonance image.
Figure 11:
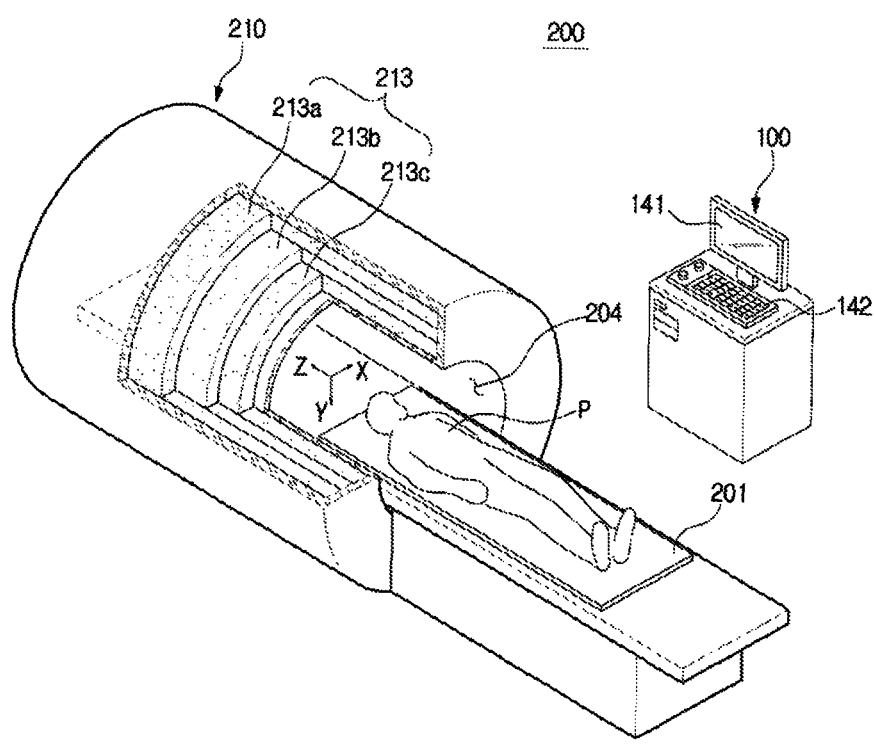
FIG. 11 is an appearance diagram illustrating a case in which a medical imaging apparatus acquires a magnetic resonance image.

FIG. 10 is a control block diagram illustrating a case in which a medical imaging apparatus acquires a magnetic resonance image, and FIG. 11 is an appearance diagram illustrating a case in which a medical imaging apparatus acquires a magnetic resonance image.

Referring to FIG. 10, when the medical imaging apparatus 200 acquires a magnetic resonance image, the scanner 210 may include a static magnetic field coil 213*a* configured to form a static magnetic field, a gradient coil 213*b* configured to apply a gradient to the static magnetic field in order to form a gradient magnetic field, and a radio frequency (RF) coil 213*c* configured to apply an RF pulse to a target object in order to excite an atomic nucleus and receive an echo signal from the atomic nucleus, and the scan control unit 220 may control movement of the patient table 201 or control an intensity and a direction of the static magnetic field, design a pulse sequence appropriate for a diagnosis part or a diagnosis purpose of a patient, and control operations of the scanner 210 according to the pulse sequence.

Referring to FIG. 11, the static magnetic field coil 213*a*, the gradient coil 213*b*, and the RF coil 213*c* are included in a magnetic assembly 213 that surrounds the bore 204.

When the patient table 201 is transported to the bore 204 in which the static magnetic field is formed, the gradient magnetic field and the RF pulse are applied to excite an atomic nucleus included in the patient P, and then an echo signal is received from the atomic nucleus, and the echo signal is used to image the inside of the target object.

Likewise, the image processing apparatus 100 may be included in the workstation, or implemented as the workstation, as shown in FIG. 10. In this case, the display unit 141 and the input unit 142 may be provided to the workstation.

The image processing unit 120 may receive an echo signal and may reconstruct the echo signal in order to generate a sectional plane image, or accumulate a plurality of sectional plane images in order to generate a three-dimensional (3D) volume data.

Figure 12:
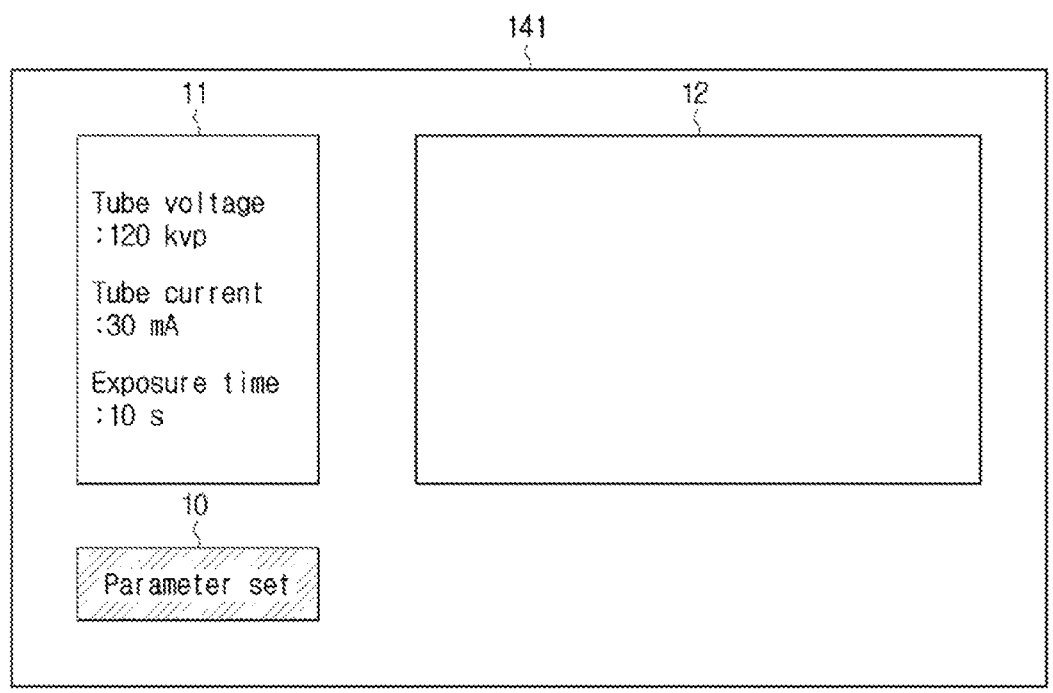
FIGS. 12 and 13 are diagrams illustrating a display unit on which a screen for setting an image processing parameter is displayed.
Figure 13:
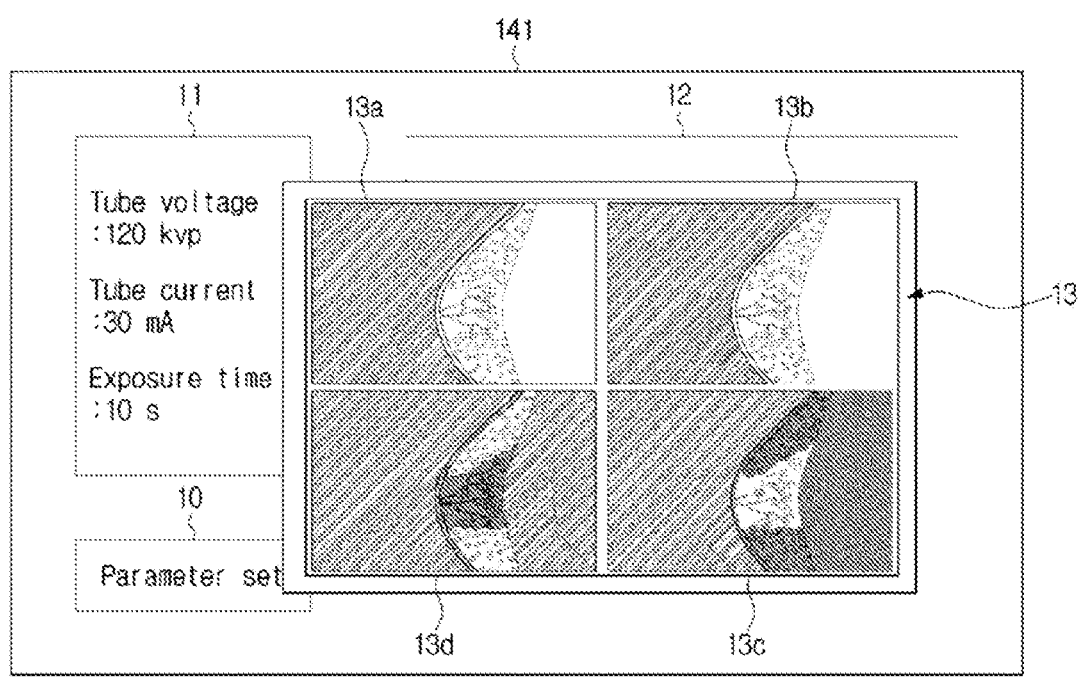

FIGS. 12 and 13 are diagrams illustrating a display unit on which a screen for setting an image processing parameter is displayed.

As shown in FIG. 12, a button 10 configured for setting the image processing parameter may be displayed on the display unit 141. When the button 10 is selected, an image processing parameter setting menu is executed. The execution of the image processing parameter setting menu may include a series of processes which enable a user to select the image processing parameter.

The button 10 may be selected by the user by adjusting the input unit 142. For example, when the input unit 142 includes a mouse or trackball, the user may select the image processing parameter setting menu by manipulating the mouse or trackball to move a pointing tool, such as a cursor displayed on a screen, and clicking the mouse or trackball when the pointing tool is positioned on the button 10. Alternatively, when the input unit 142 may be implemented as a touch panel, the user may select the image processing parameter setting menu by touching a position corresponding to the button on the touch panel.

A window 11 that includes a list of scan parameters applied or to be applied to scan of a patient may be displayed on the display unit 141, and a final medical image on which the image processing has been performed may be displayed in a medical image window 12. However, such a screen configuration is merely an example. As long as a button for executing the image processing parameter setting menu is displayed, the remaining aspects of the screen configuration may be changed.

A screen as shown in FIG. 12 may be displayed whenever the image processing apparatus 100 is booted, upon initial installation, by periods, or whenever a new medical image is acquired. Alternatively, when the image processing apparatus 100 is in an on state, a button for executing an image processing parameter setting menu may be always displayed on one side of the display unit 141. Alternatively, a button for executing an entire setting menu of the image processing apparatus 100 may be displayed, and settable items including an image processing parameter may be displayed when the button is selected. In particular, when the image processing parameter setting menu is selected, a configuration of a screen displayed on the display unit 141 is not specially limited.

When the button 10 is selected in order to execute an image processing parameter setting menu, as shown in FIG. 13, a pop-up window 13 which includes a plurality of sample images 13*a*, 13*b*, 13*c*, and 13*d* is displayed. In an example of FIG. 13, four breast images are used as the plurality of sample images. However, the types or number of sample images is not limited. The types of the sample images may be determined according to or irrespective of the type of medical image processed by the image processing apparatus 100. In addition, the number of sample images may be set or changed by a user.

The plurality of sample images 13a, 13b, 13c, and 13d are obtained by performing different respective image processing operations. Specifically, when the image processing parameter setting menu is executed, the image processing unit 120 performs image processing operations in order to generate a plurality of sample images. In this case, different image processing operations are performed with respect to the respective sample images.

The parameter control unit 110 may control an image processing parameter applied for the image processing unit 120 in order to generate the sample image. As described above, data that relates to a preference for the image processing parameter may be stored in the storage unit 130. For example, a plurality of sample images that are generated first after the image processing parameter setting menu is set may be processed according to statistical data stored in the storage unit 130. In particular, the image processing may be performed according to a parameter combination generally preferred by many users.

The four sample images 13a, 13b, 13c, and 13d may have all or some of image processing parameters that are set to values which are different from those of the other sample images. Whether the image processing parameters applied to the respective sample images are different is not limited. However, a combination of the image processing parameters applied to one sample image may vary.

As will be described below, when a user selects parameters to finally converge into the most preferred parameter combination, the user may use a learning result which relates to data stored in the storage unit 130. For this purpose, the parameter control unit 110 may include a learning module configured to perform machine learning with respect to the data stored in the storage unit 130 and a determination module configured to determine an optimized image processing parameter based on a learning result obtained by the learning module.

The machine learning is one field of artificial intelligence and denotes a process of enabling a computer to extract useful knowledge from accumulated data and draw a determination based on the extracted useful knowledge. The machine learning has a generalization capacity, which denotes processing with respect to new data that is input via a representation that evaluates data. There are various algorithms according to an approach of the machine learning, and as an example, an artificial neural network may be used.

The artificial neural network is obtained by modeling a structure of a human brain in which efficient recognition actions occur and are implemented as hardware, software, or a combination thereof. A human brain is composed of neurons, which are a basic unit of a nerve cell and which are connected via synapses to process information non-linearly and in parallel. A human brain performs learning while adjusting a connection form or connection intensity of synapses. In this aspect, the brain adjust the connection intensity of the synapses by weakening a connection between neurons that lead to a wrong answer and strengthening a connection between neurons that lead to a correct answer.

As an example, a determination module that is learned by the learning module may include a deep neural network having a multilayer structure. The deep neural network is an example of the artificial neural network. The deep neural network has one or more hidden layers between an input layer and an output layer. Each layer may be formed of a plurality of nodes that correspond to artificial neurons, and a connection relation between nodes in different layers may be determined by learning. For example, only nodes included in adjacent layers may be connected according to a structure of a restricted Boltzmann machine (RBM). As such, learning performed by the learning module applying the deep neural network may be referred to as deep learning. When the learning module generates a determination module by using the deep learning, the determination module may have a structure of the above-described artificial neural network.

The learning module of the parameter control unit 110 may learn the data stored in the storage unit 130 according to the above-described methods. However, this is merely an example, and the data may be learned by applying any of various machine learning methods other than the above-described method.

Figure 14:
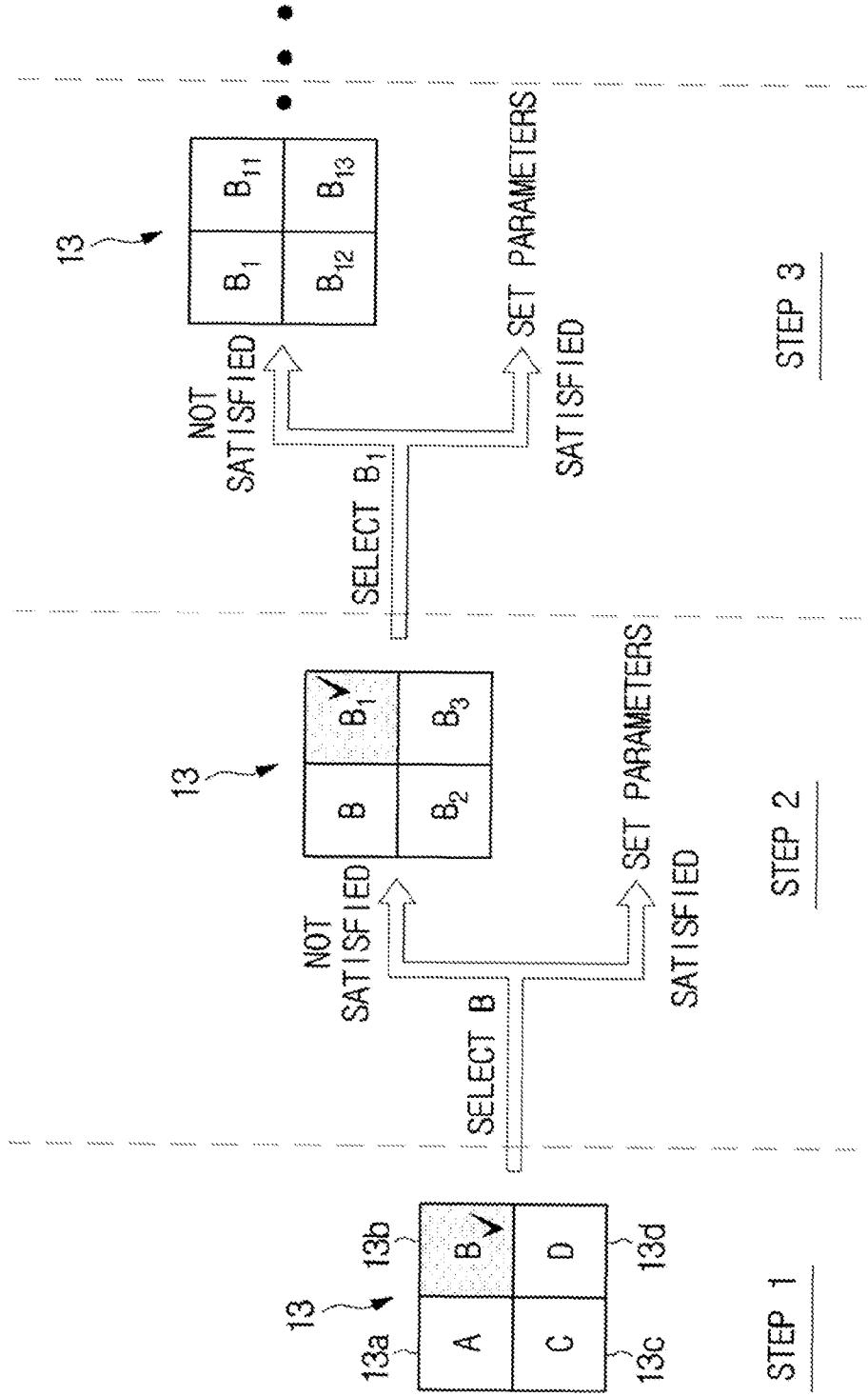
FIG. 14 is an exemplary diagram schematically illustrating a process of a user selecting one of a plurality of sample images.

FIG. 14 is an exemplary diagram schematically illustrating a process of a user selecting one of a plurality of sample images.

In an example of FIG. 14, it is assumed that a plurality of sample images are referred to as sample image A, sample image B, sample image C, and sample image D according to a combination of the image processing parameters. In a screen as shown in FIG. 13, in a condition that a user selects the sample image B (i.e., step 1 as illustrated on the left side of FIG. 14), when the user is satisfied with the selected sample image B, the user ends the image processing parameter setting menu and sets image processing parameters according to the selected sample image B (i.e., lower option of step 2 as illustrated at center portion of FIG. 14). For this purpose, when the user selects one of the sample images, a pop-up window may be displayed on the display unit 141 to inquire about whether to set parameters. In this aspect, the setting of the image processing parameters denotes storing values of the image processing parameters that are to be applied when a medical image is subsequently processed.

When the user is not satisfied with the sample image B, the display unit 141 may display new sample images (i.e., upper option of step 2 as illustrated at center portion of FIG. 14). To this end, the image processing unit 120 may perform new image processing operation(s) with respect to the same image. In this case, the image processing parameter applied to the new image processing operation(s) may be determined based on learning of the parameter control unit 110 and the sample image selected in a previous step (step 1). For example, when the image processing parameters applied to the sample image selected in the previous step are input to the determination module formed by the learning of the parameter control unit 110, a combination of the image processing parameters determined in consideration of a current user's preference may be output. In particular, the determination module may optimize the image processing parameter. In this exemplary embodiment, a process of the determination module determining the image processing parameters may be defined as optimization of the image processing parameters, and the image processing parameters determined by the determination module may be defined as image processing parameters optimized in consideration of a user's preference.

The image processing unit 120 may perform image processing operation(s) according to the output combination of the image processing parameters. As an example, if the sample image B selected in the previous step is an image having high contrast, the image processing unit 120 may minimize a variation in the contrast to keep the high contrast, and change other image processing parameters to generate sample image $B_1$, sample image $B_2$, and sample image $B_3$. When the plurality of sample images are displayed in step 2, the sample image B selected by the user in step 1 may also by displayed.

When the user selects the sample image $B_1$ in step 2 and is satisfied with the sample image $B_1$, the user ends the image processing parameter setting menu and sets the parameter according to the sample image $B_1$ (i.e., lower option of step 3 as illustrated on the right side of FIG. 14).

However, when the user is still not satisfied with the sample image $B_1$, the display unit 141 may display additional new sample images (i.e., upper option of step 3 as illustrated on the right side of FIG. 14). To this end, the image processing unit 120 may perform new image processing operation(s) on the same image. In this case, the image processing parameter applied to the new image processing operation(s) may be determined based on learning of the parameter control unit 110 and the sample image $B_1$ selected in a previous step (step 2). The details are the same as described above.

As an example, sample image $B_{11}$, sample image $B_{12}$, sample image $B_{13}$ may be generated and displayed in step 3 by minimizing a variation in a specific image processing parameter applied to the sample image $B_1$ selected in the previous step (step 2) and changing the other image processing parameters.

Likewise, when the user selects one of the displayed sample images, the user may go to the next step or set the image processing parameters depending on whether the user is satisfied with the selected sample image. Accordingly, it is possible to gradually converge into an image processing parameter combination based on a current user's preference by showing sample images via several steps and prompting the user to select a desired image in each step and applying a selection of the user to a learning result to generate sample images in a next step.

When the user is satisfied with the selected sample image and ends the image processing parameter setting menu, the parameter control unit 110 may set an image processing parameter based on a finally selected sample image. For example, the parameter control unit 110 may input the image processing parameter combination applied to the finally selected sample image to the determination module, output an optimal image processing parameter combination, which is preferred by the user, and set image processing parameters according to the output image processing parameter combination.

As another example, the parameter control unit 110 may set image processing parameters by using values of the image processing parameters applied to the finally selected sample image without applying the learning.

Figure 15:
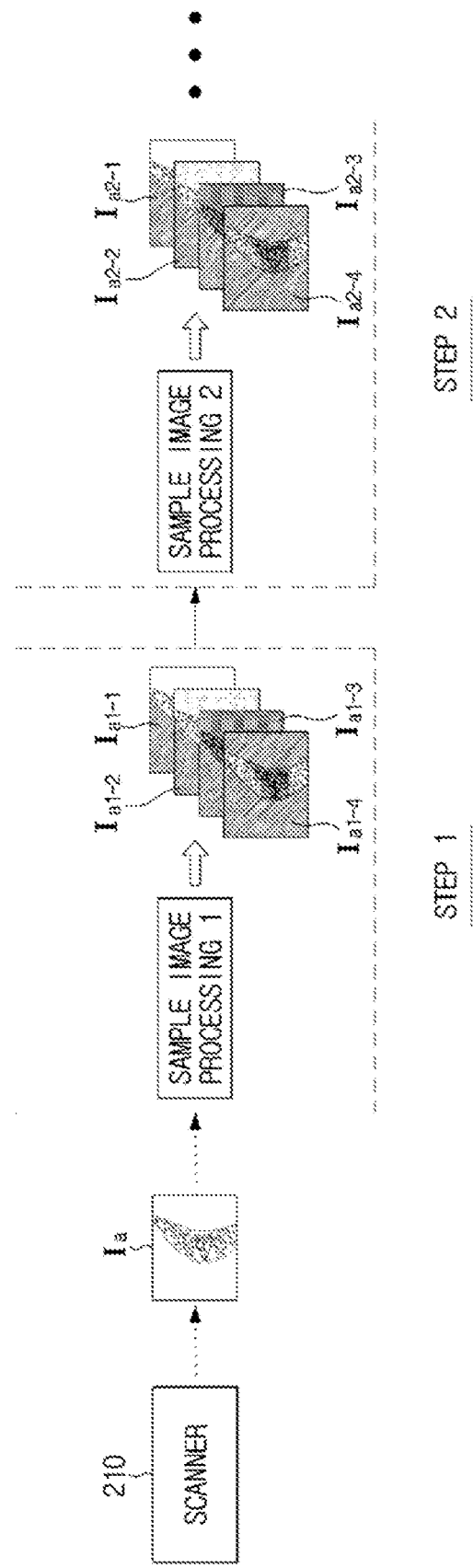
FIGS. 15 and 16 are diagrams illustrating a method of providing a sample image.
Figure 16:
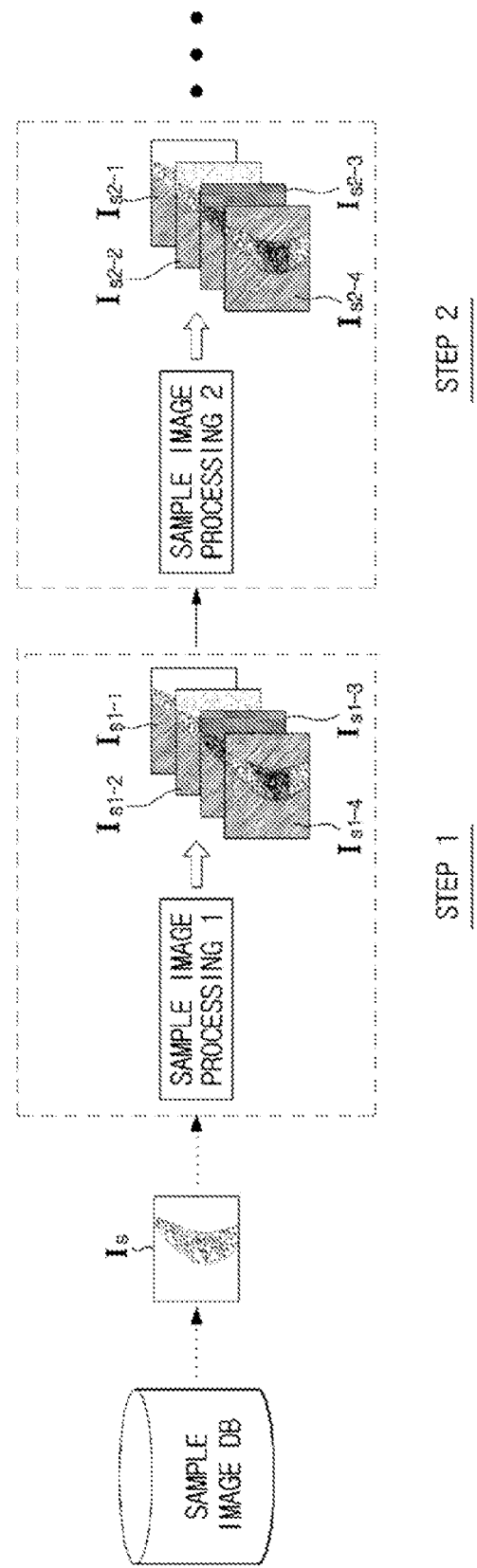

FIGS. 15 and 16 are diagrams illustrating a method of providing a sample image.

As shown in FIG. 15, an image used for the image processing unit 120 to perform image processing to generate sample images may be a medical image $I_a$ acquired by the scanner 210. This image is a main image to which a set image processing parameter is to be applied.

In step 1, sample image processing 1 is performed on the medical image $I_a$ in order to generate and display a plurality of sample images $I_{a1-1}$, $I_{a1-2}$, $I_{a1-3}$, and $I_{a1-4}$. When the image processing parameter setting menu is not ended, sample image processing 2 is performed on the sample image selected in step 1 in order to generate and display a plurality of sample images $I_{a2-1}$, $I_{a2-2}$, $I_{a2-3}$, and $I_{a2-4}$. The step may be repeated until the user is satisfied with the selected sample image. As such, when the sample images are generated by using a main image to which the image processing is actually to be applied, the user may select the image processing parameters more intuitively.

Alternatively, as shown in FIG. 16, image processing may be performed on an image $I_s$ stored in a sample image database (DB) in order to generate a sample image. The sample image DB may be stored in the storage unit 130, stored in a memory provided in the medical imaging apparatus 200 separately from the storage unit 130, or stored in another external server. An image to be used for sample image processing may be selected from the sample image DB arbitrarily, selected by a user, and/or selected automatically according to the type of the main image on which the image processing apparatus 100 will perform image processing. For example, when the image processing apparatus 100 performs image processing with respect to a magnetic resonance image of a brain, the image processing apparatus 100 may select the magnetic resonance image of the brain from among the images stored in the sample image DB.

In step 1, sample image processing 1 is performed on the medical image $I_s$ in order to generate and display a plurality of sample images $I_{s1-1}$, $I_{s1-2}$, $I_{s1-3}$, and $I_{s1-4}$. When the image processing parameter setting menu is not ended, sample image processing 2 is performed on the sample image selected in step 1 in order to generate and display a plurality of sample images $I_{s2-1}$, $I_{s2-2}$, $I_{s2-3}$, and $I_{s2-4}$. The step may be repeated until the user is satisfied with the selected sample image. As such, when the image stored in the sample image DB is used, the sample image may be generated even when the main image is not yet acquired, such as upon initial execution.

Figure 17:
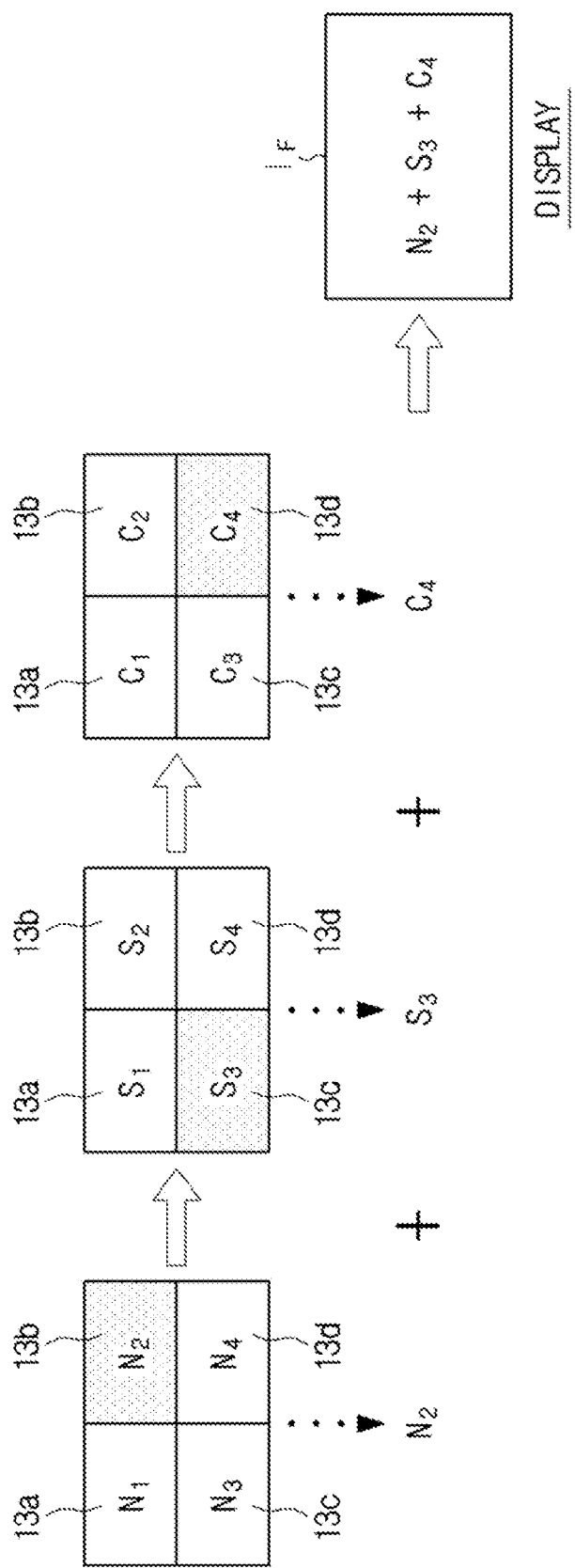
FIGS. 17 and 18 are diagrams schematically illustrating a process of a user selecting one of a plurality of sample images.
Figure 18:
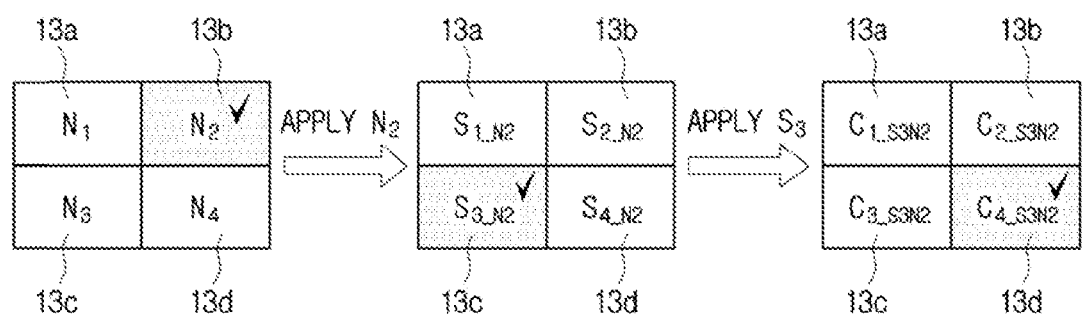

FIGS. 17 and 18 are diagrams schematically illustrating a process of a user selecting one of a plurality of sample images.

In the above-described example of FIG. 14, the display unit 141 may display sample images on which different image processing operations have been performed via several steps and prompt a user to select one of the sample images, thereby gradually converging into an optimal image processing parameter combination that is preferred by the user. However, as shown in FIGS. 17 and 18, a specific image processing parameter may be selected in each step. This will be described below in detail.

In an example of FIGS. 17 and 18, it is assumed that noise, contrast, and sharpness, which are representative image processing parameters, are selected. First, referring to FIG. 17, a plurality of sample images displayed on the pop-up window 13 of the display unit 141 may include sample image $N_1$, sample image $N_2$, sample image $N_3$, and sample image $N_4$ to which a noise parameter is variably applied. Other than noise, the same parameter values are applied to the images. Alternatively, a value optimized with respect to the noise parameter value, that is, a value determined according to the noise parameter value, is applied to the images. In this step, when the user selects the sample image $N_2$, the noise parameter is set according to the selected sample image $N_2$. In this case, the noise parameter may also reflect a user's preference.

In the next step, sample image $S_1$, sample image $S_2$, sample image $S_3$, and sample image $S_4$ to which a sharpness parameter has been applied variably may be displayed. Other than sharpness, the same parameter values are applied to the images. Alternatively, a value determined according to the sharpness parameter value may be applied to the images. In this step, when the user selects the sample image $S_3$, the sharpness parameter is set according to the selected sample image $S_3$. In this case, the sharpness parameter may also reflect a user's preference.

In the next step, sample image $C_1$, sample image $C_2$, sample image $C_3$, and sample image $C_4$ to which a contrast parameter has been applied variably may be displayed. Other than contrast, the same parameter values are applied to the images. Alternatively, a value determined according to the contrast parameter value may be applied to the images. In this step, when the user selects the sample image $C_4$, the contrast parameter is set according to the selected sample image $C_4$. In this case, the contrast parameter may also reflect multiple users' preferences stored in the storage unit 130.

When the display and selection of the sample images for each parameter are completed, a final sample image that is based upon all of the user's selections may be displayed to receive a confirmation as to whether the user is satisfied with the image. If the noise parameter value applied to the sample image $N_2$ is $N_2$, the sharpness parameter value applied to the sample image $S_3$ is $S_3$, and the contrast parameter value applied to the sample image $C_4$ is $C_4$, all of $N_2$, $S_3$, and $C_4$ may be applied to a final sample image. When the user is satisfied with the final sample image, $N_2$, $S_3$, and $C_4$ are set to respective parameter values. When the user is not satisfied with the final sample image, an image processing process, a sample image display process, and a user selection process are repeatedly performed.

Alternatively, the learning of the parameter control unit 110 may be applied instead of setting the image processing parameters applied to the selected sample image without change as described above. In this case, the image processing parameter values $N_2$, $S_3$, and $C_4$ may be inputted to the determination module, and when image processing parameter values determined by the determination module are output, a final sample image on which image processing has been performed by applying the image processing parameter values may be displayed. Alternatively, $N_2$, $S_3$, and $C_4$ are applied to the final sample image without change, and when the user selects the final sample image, values optimized by applying the learning may be set to the parameters.

In the above-described example of FIG. 17, a selection of the user in the previous step is not reflected in the sample image displayed in the current step. However, as shown in FIG. 18, the selection of the user in the previous step may be reflected in the sample image displayed in the current step.

In particular, when the user selects the sample image $N_2$, a noise parameter of $N_2$ is applied to a sample image generated in the next step in order to generate sample image $S_{1\_N2}$, sample image $S_{2\_N2}$, sample image $S_{3\_N2}$, and sample image $S_{4\_N2}$. In addition, when the user selects the $S_{3\_N2}$ in the next step, a sharpness parameter of $S_3$ is applied to the sample image generated in the next step in order to generate sample image $C_{1\_S3N2}$, sample image $C_{2\_S3N2}$, sample image $C_{3\_S3N2}$, and sample image $C_{4\_S3N2}$. In this case, although the final sample image is generated and displayed separately, a sample image selected in the current step may be the final sample image. For example, as shown in FIG. 18, when the user selects the sample image $C_{4\_S3N2}$, the user may use the sample image $C_{4\_S3N2}$ to determine whether to execute an addition step because all parameters selected by the user are reflected in the sample image $C_{4\_S3N2}$.

Likewise, in an example of FIG. 18, the learning of the parameter control unit 110 may also be applied. In this case, the image processing parameter values $N_2$, $S_3$, and $C_4$ may be inputted to the determination module formed via the learning, and when image processing parameter values which are determined, i.e., optimized, by the determination module are output, a final sample image to which the optimized image processing parameter values have been applied may be displayed. Alternatively, $N_2$, $S_3$, and $C_4$ may be applied to the final sample image without change, and when the user selects the final sample image, the optimized values may be set to the parameters.

After setting the image processing parameter(s) according to the above-described method, the user may change the image processing parameter(s). For example, the user may set image processing parameters using the image $I_s$ stored in the sample image DB when the image processing apparatus 100 is powered on, but later the user may desire to change or reset the image processing parameters because the user may not be satisfied with a result of performing image processing with respect to a medical image received from the scanner 210. An exemplary embodiment which relates to changing or resetting the parameters will be described below.

Figure 19:
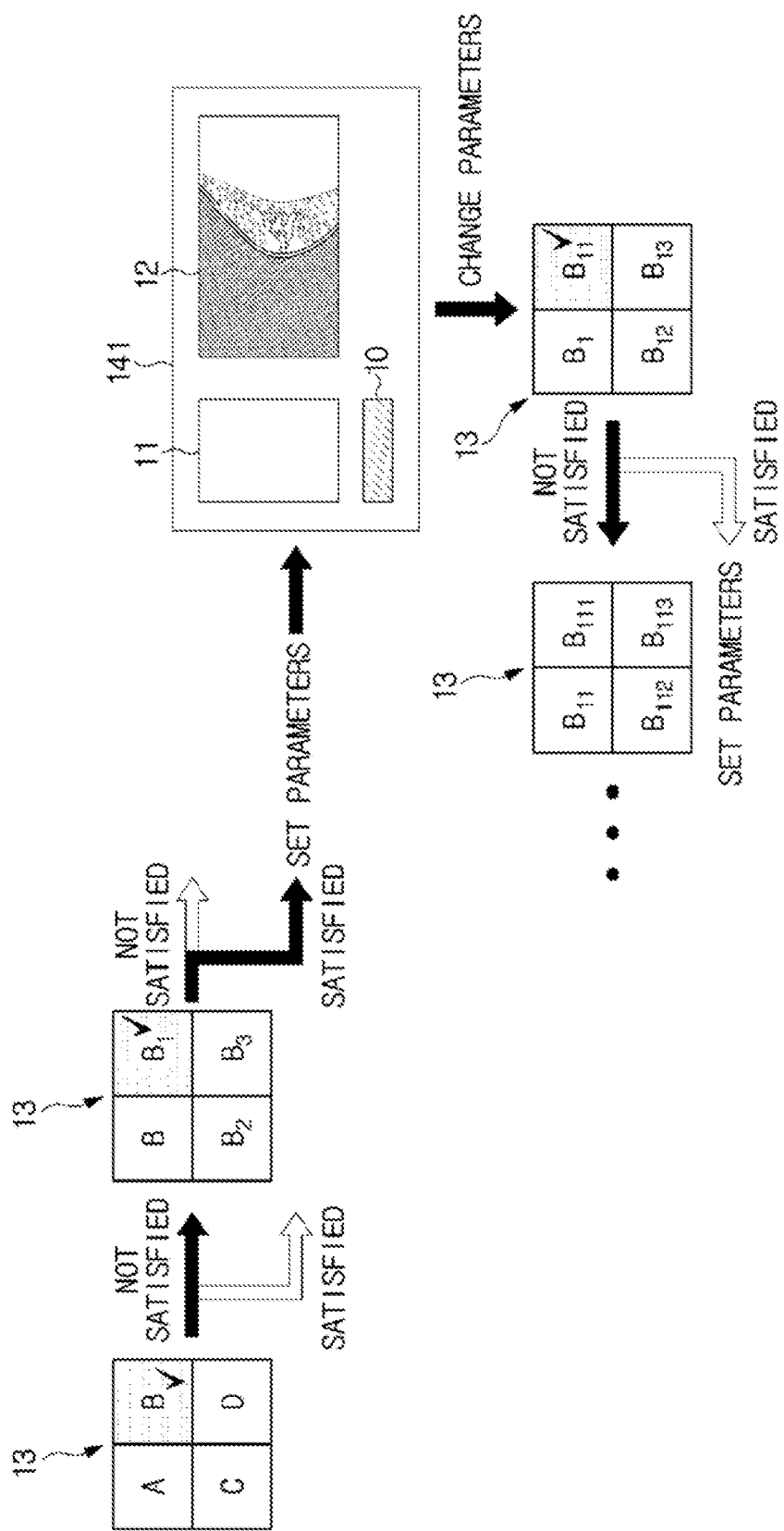
FIGS. 19 and 20 are diagrams illustrating a process of changing an image processing parameter that has previously been set.
Figure 20:
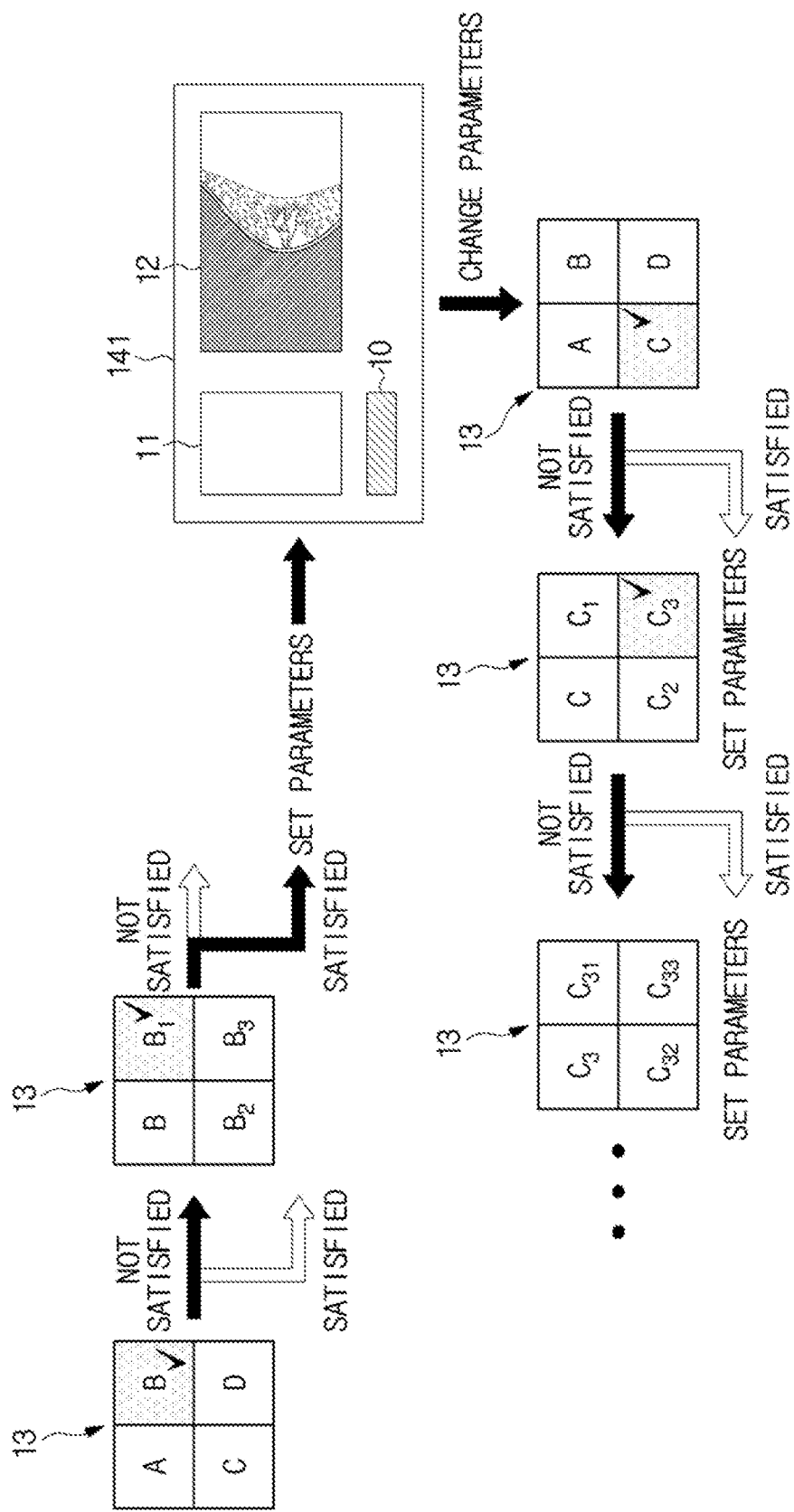

FIGS. 19 and 20 are diagrams illustrating a process of changing an image processing parameter that has previously been set. In an example of FIGS. 19 and 20, it is assumed that the parameter is set by gradually converging into an image processing parameter combination that is desired by the user as indicated by selections made in several steps, as shown in the example of FIG. 14.

In addition, in the example of FIGS. 19 and 20, it is assumed that the sample image the user finally selects is sample image $B_1$, and image processing parameters are set based on an image processing parameter combination applied to the sample image $B_1$ and learning of the parameter control unit 110. When a final medical image on which image processing is performed by applying the set parameters is displayed on the medical image window 12, but the user is not satisfied with the parameters and desires to change the parameters, the user may reselect the button 10 for executing the image processing parameter setting menu that is displayed on the display unit 141 in order to request a change of the parameters. Alternatively, a button for changing parameters may be further displayed independently of setting of the parameters.

When the button 10 is selected, the pop-up window 13 which includes a plurality of sample images is displayed on the display unit 141. As shown in FIG. 19, this step may be connected with setting of the image processing parameters that had been performed most recently. In particular, when the user selected the sample image $B_1$ in the setting of the image processing parameter that had been performed most recently, a step that is executed to change parameters is a next step of a case in which the user selects, but is not satisfied with, the sample image $B_1$. That is, upon setting image processing parameters, the user optimizes the image processing parameters applied to the finally selected sample image again by applying the image processing parameters to the determination module. Accordingly, the image processing unit 120 may perform image processing in order to generate sample image $B_{11}$, sample image $B_{12}$, and sample image $B_{13}$, and the display unit 141 may display the sample image $B_{11}$, sample image $B_{12}$, and sample image $B_{13}$ in addition to the sample image $B_1$.

When the user selects, but is not satisfied with, the sample image $B_{11}$, the image processing unit 120 may perform image processing in order to generate sample image $B_{111}$, sample image $B_{112}$, and sample image $B_{113}$, and the display unit 141 may display the sample image $B_{111}$, sample image $B_{112}$, and sample image $B_{113}$ in addition to the sample image $B_{11}$. As above described, the sample image $B_{111}$, sample image $B_{112}$, and sample image $B_{113}$ may have an image processing parameter combination that is determined based on the sample image $B_{11}$ and the learning of the parameter control unit 110.

Alternatively, as shown in FIG. 20, even when the user changes the previously set parameters, the process of setting parameters may be executed from the beginning again. Accordingly, when the user selects the button 10, a series of processes of displaying sample image A, sample image B, sample image C, and sample image D again, receiving a selection from a user, receiving a confirmation whether the user is satisfied, and setting parameters or proceeding to a next step may be performed again. When the sample image displayed on the display unit 141 in order to prompt the selection of the user is generated by processing an image stored in the sample image DB, and a result of applying the set image processing parameters to a main image has a difference with a sample image, in an example shown in FIG. 20, it is possible to more accurately reflect a user's preference by starting anew from an initial step of the parameter setting process.

Alternatively, the parameters may not be changed by displaying the sample images and selecting one of the sample images by the user as shown in an example of FIGS. 19 and 20, but instead by the user directly adjusting the image processing parameter values.

The parameters currently set or changed by a user may be included in learning data of a learning module. In particular, all image processing parameters that are set or changed by the user may be stored in a parameter DB of the storage unit 130, and the learning module of the parameter control unit 110 may learn data stored in the parameter DB. Accordingly, a learning result may be updated whenever the image processing parameter is set or changed, and thus an algorithm of the determination module or a structure of an artificial neural network may be changed.

In the above-described exemplary embodiment, the user is allowed to select image processing parameters via several steps, and the learning of the parameter control unit 110 is applied before the next step, thereby gradually converging into an optimized parameter that is preferred by the user. In another example of the image processing apparatus 100, the image processing parameters are set once in an initial step and then a learning result is applied whenever the parameters are changed by the user, thereby converging into optimized image processing parameters. This will be described with reference to FIG. 21.

Figure 21:
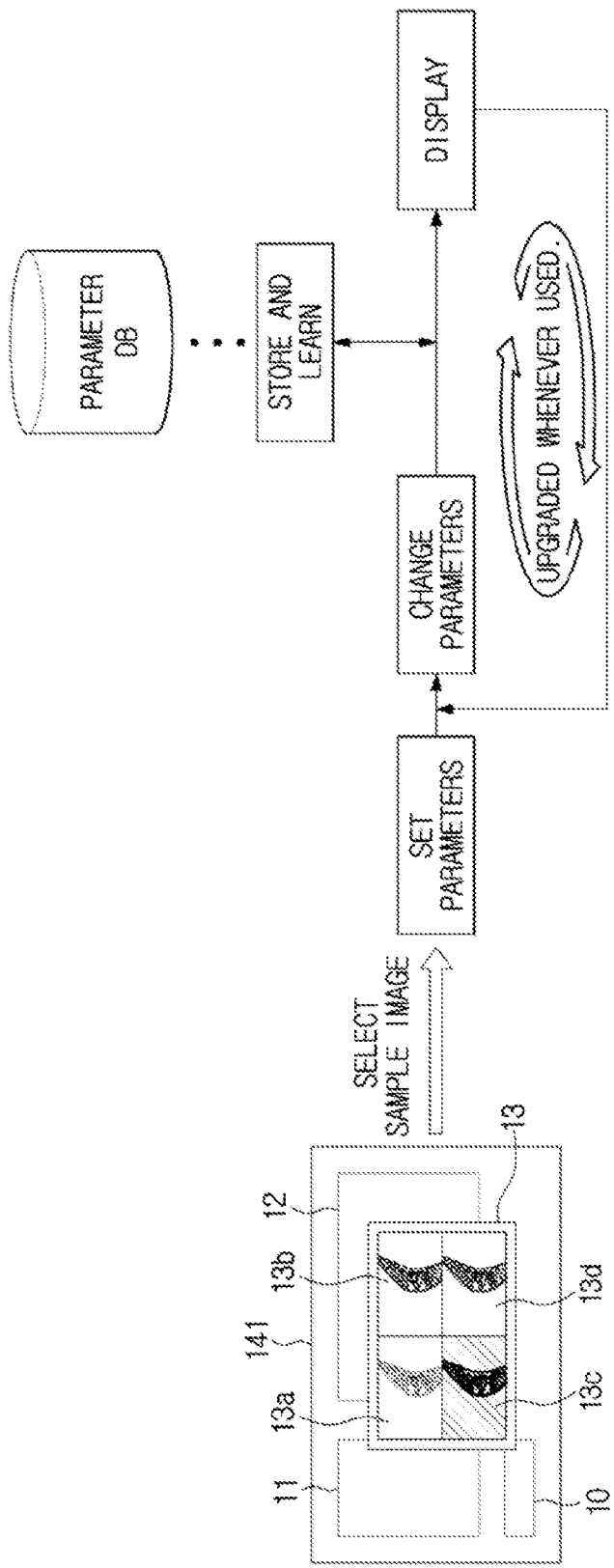
FIG. 21 is a diagram illustrating an example of setting an image processing parameter once in an initial step and then applying learning whenever the parameter is changed by a user.

FIG. 21 is a diagram illustrating an example of setting an image processing parameter once in an initial step and then applying learning whenever the parameter is changed by a user.

Referring to FIG. 21, when the plurality of sample images 13a, 13b, 13c, and 13d are displayed on the display unit 141, the user may select the most preferred sample image from among the displayed images and set initial image processing parameters based on the selected sample image. Parameters applied to the selected sample image may be set without change, or may be optimized, based on learning of the parameter control unit 110.

The setting of the initial image processing parameters may be accomplished upon first powering-up of the image processing apparatus 100 and/or periodically. Description of the displayed sample images is the same as described above.

Even when the initial image processing parameters are set, the user may change the parameters while using the image processing apparatus 100, and the changed parameters may be stored in the parameter DB. When the parameters are changed, the parameter control unit 110 may apply the learning to the changed parameters in order to optimize the image processing parameters, and may apply the optimized image processing parameters when the next image is displayed. Accordingly, as the frequency of use increases, the image processing parameter may be gradually optimized appropriately to the user's preference.

The learning module of the parameter control unit 110 may include data stored in the parameter DB in the learning data, and may perform the learning whenever a new parameter is stored in the parameter DB. Accordingly, the learning result may be updated whenever the parameters are changed, and the learning data is accumulated as the frequency of use increases, thus gradually optimizing the image processing parameters appropriately to the user's preference.

Figure 22:
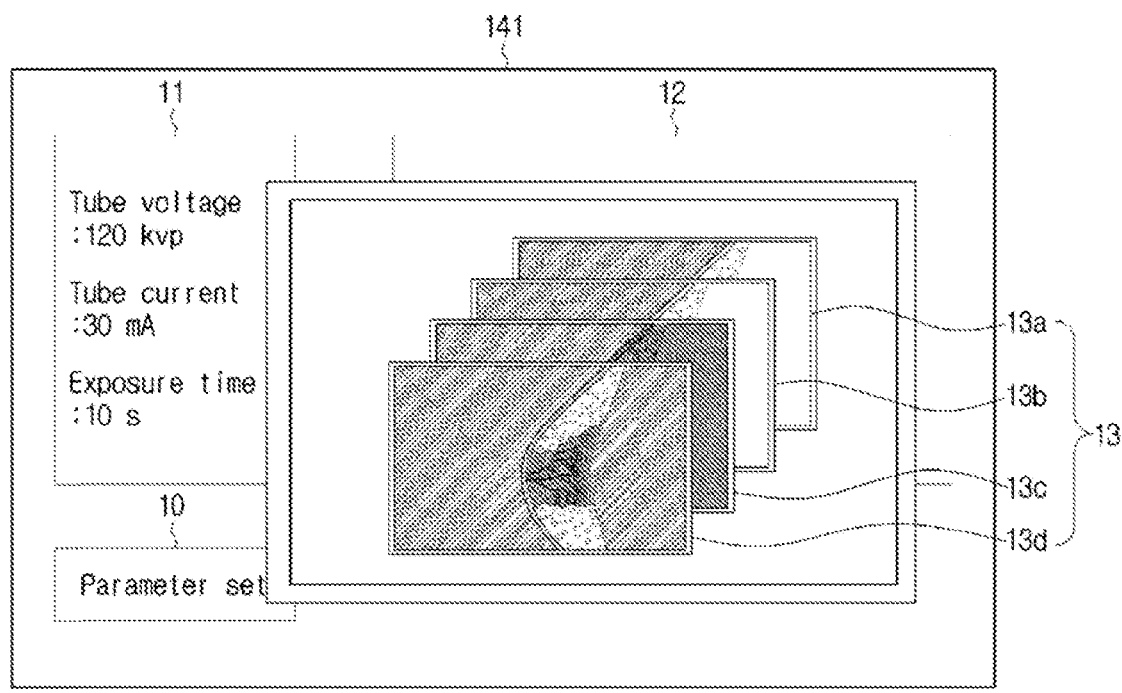
FIGS. 22 and 23 are diagrams illustrating another example of providing a plurality of sample images to a user.
Figure 23:
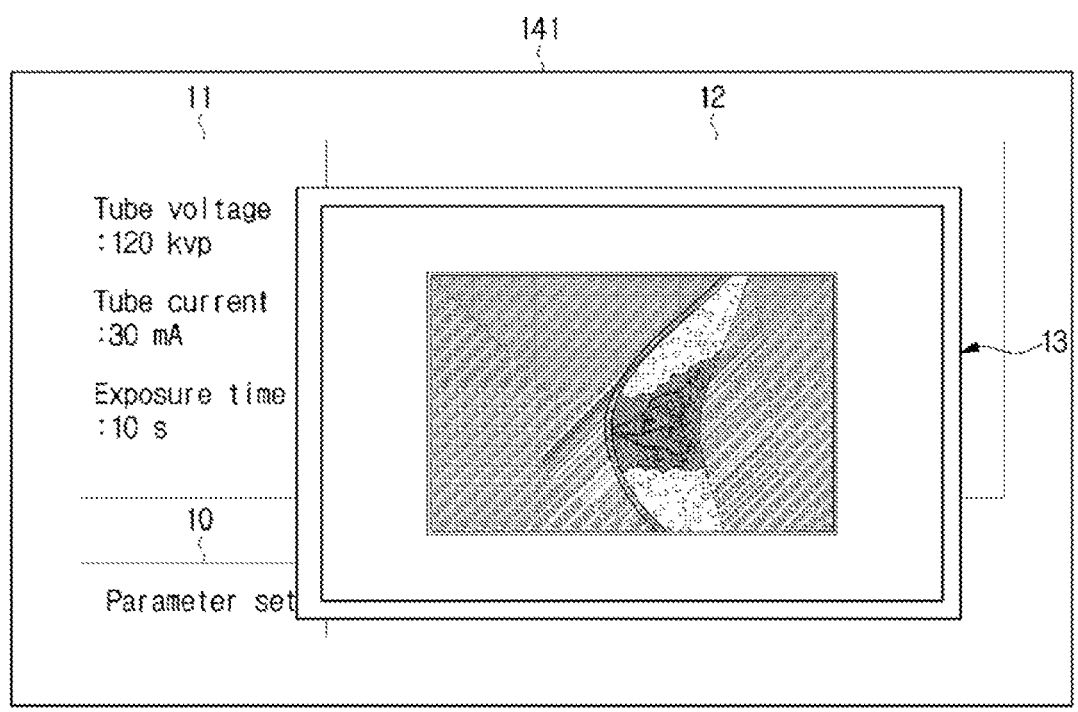

FIGS. 22 and 23 are diagrams illustrating another example of providing a plurality of sample images to a user.

In the above-described example, a plurality of sample images are simultaneously displayed without overlapping each other. However, an exemplary embodiment of the image processing apparatus 100 is not limited thereto. As described in FIG. 22, the plurality of sample images 13a, 13b, 13c, and 13d may be arranged in front and rear within the pop-up window 13, and rear images may be partially covered by front images. In this case, when the user selects a specific sample image, the selected sample image may be moved to the forefront and be shown without covered parts. When the input unit 142 is implemented as a touch panel, the user may select a desired sample image by touching and then swiping or dragging the sample image to the front side. In addition, when the input unit 142 is implemented as a mouse or trackball, the user may select a desired sample image by simply clicking the sample image.

Alternatively, as shown in FIG. 23, the plurality of sample images 13a, 13b, 13c, and 13d may be displayed at the same position but at different times. This is referred to as toggling. For example, when the images are switched at certain intervals, a first image 13a is displayed and then switched to a second image 13b after time t. The second image 13b is switched to a third image 13c after time t, and subsequently the third image 13c is switched to a fourth image 13d after time t. In this case, since the images are switched at the same position, differences between the images may be maximally displayed.

Figure 24:
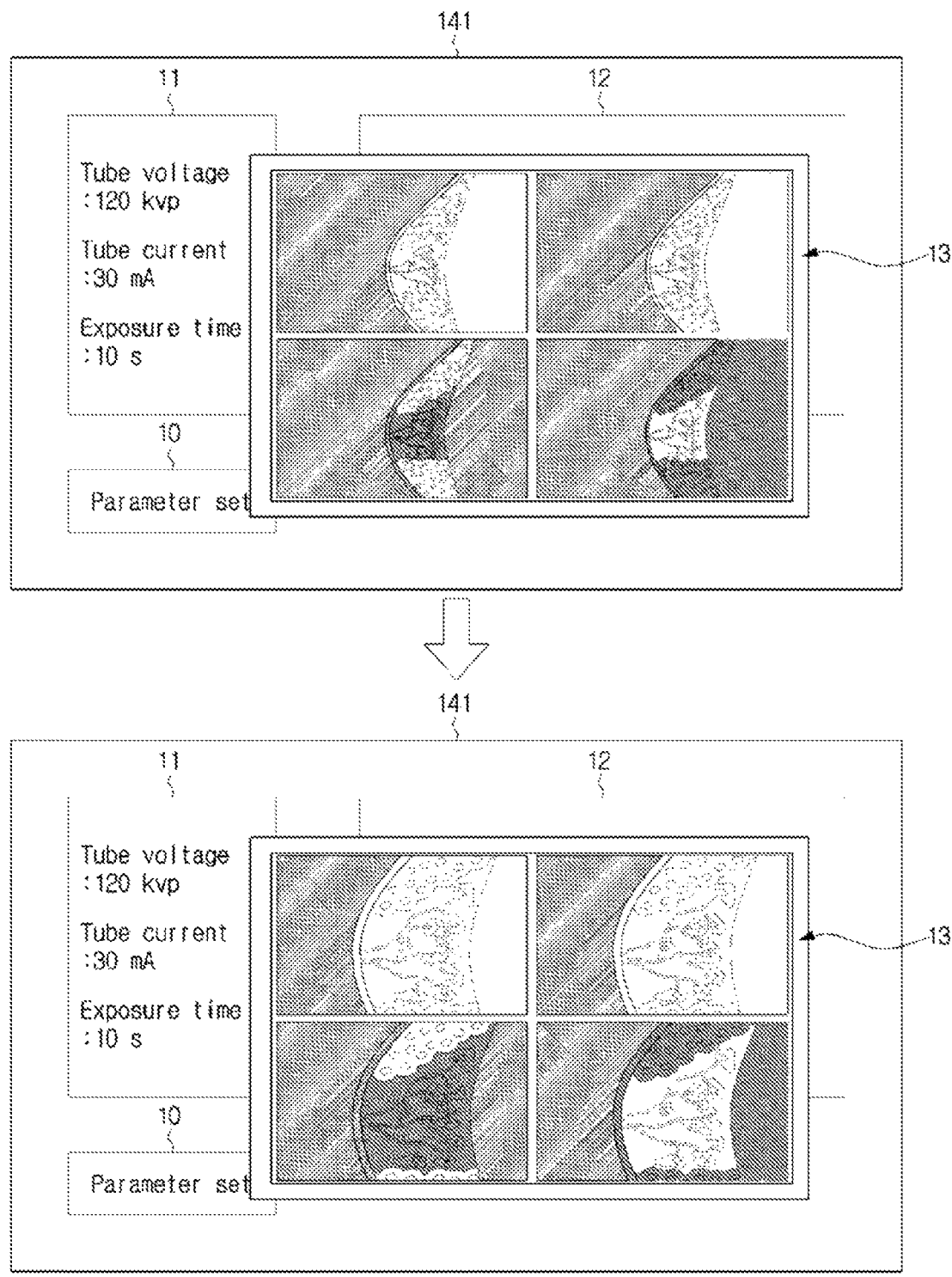
FIG. 24 is a diagram illustrating an example of enlarging and displaying a portion of a sample image.

FIG. 24 is a diagram illustrating an example of enlarging and displaying a portion of a sample image.

As shown in FIG. 24, the plurality of sample images 13a, 13b, 13c, and 13d are displayed on the display unit 141, and when a user selects a part of the displayed sample images, the selected part may be enlarged and displayed. The selection of a part of the displayed sample images may be accomplished via a touch or click of a corresponding region according to the type of the input unit 142. For example, when the user has already known a part which is deemed to correspond to a lesion of a patient, the user may select and enlarge a corresponding position in a sample image, and may determine which image processing parameters are appropriate to be applied in order for the user to see the enlarged image to check the lesion.

Figure 25:
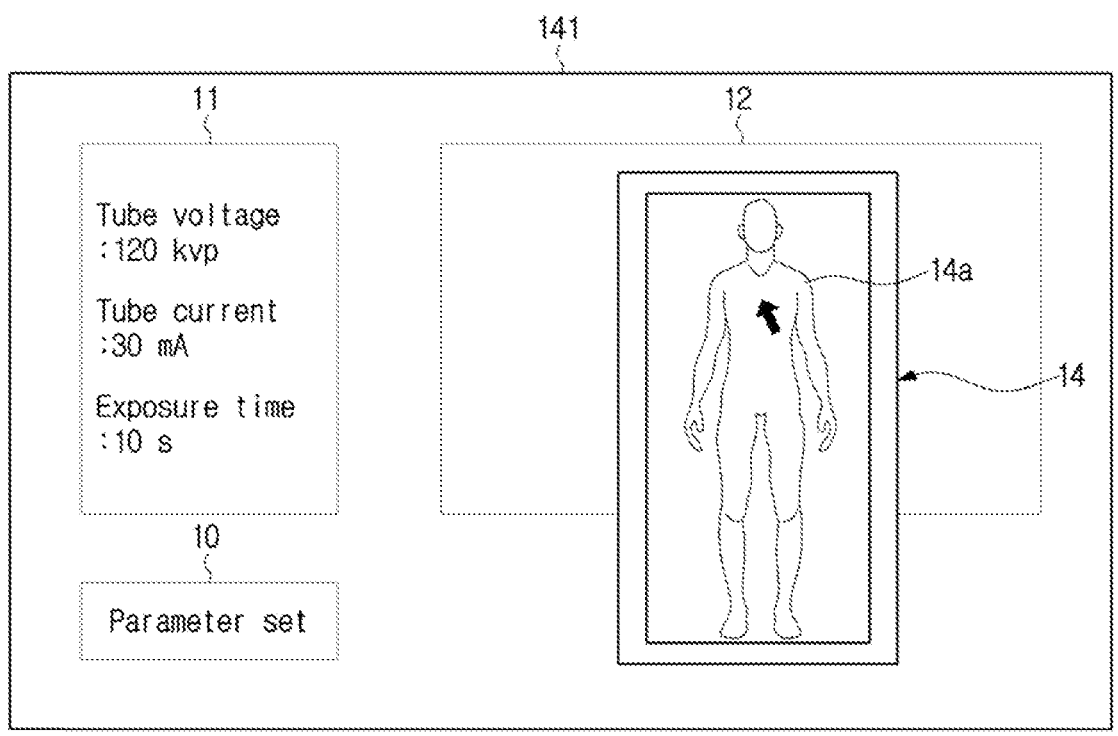
FIG. 25 is a diagram illustrating an example of setting an image processing parameter for each human part.

FIG. 25 is a diagram illustrating an example of setting an image processing parameter for each human part.

The image processing parameters may be set for each respective part of the human body when the image processing apparatus 100 is included in the medical imaging apparatus 200 and the medical imaging apparatus 200 scans several parts of a human body, like general radiography, or when the image processing apparatus 100 is included in the central server 300 or the user computer 400 and processes images acquired by several medical imaging apparatuses.

A respective tissue characteristic may be different for each respective human part, and an image characteristic may be different when the tissue characteristic is different. For example, some tissues may be associated with high noise in a medical image, and some tissues may be associated with low contrast in the medical image. Accordingly, the tissues associated with high noise may be focused on decreasing the noise in the corresponding image, and the tissues associated with low contrast may be focused on increasing the contrast in the corresponding image.

As shown in FIG. 25, a pop-up window 14 including a feature 14a of a human body may be displayed on the display unit 141 before the image processing parameters are set such that a part for which the parameters are intended to be set may be selected. A user may perform the selection by touching or clicking the part for which the parameters are intended to be set in the displayed feature 14a of the human body. As such, when the image processing parameters are set and managed independently for each human part, image processing may be performed optimally for characteristics of the scan target as well as the user's preference.

In addition, since the image processing apparatus 100 may be shared by a plurality of users, the image processing parameters may be set and managed for each user. For example, when the image processing apparatus 100 is included in the medical imaging apparatus 200 or the central server 300, a plurality of users share the image processing apparatus 100. An account may be allocated to each user, and the user may log in to the allocated account and access information which relates to image processing parameters of the user when using the image processing apparatus 100. The setting and changing of the image processing parameters that are performed after the log-in to the account may be applied only to the corresponding user. In addition, the user may also log in to the account using the user computer 400 to share the image processing parameters that are set and managed by the image processing apparatus 100. However, an exemplary embodiment of the image processing apparatus 100 is not limited thereto, and the image processing parameters may be set and managed for each user by using any of various other methods.

An exemplary embodiment of an image processing method will be described below.

The image processing apparatus 100 according to the above-described exemplary embodiment may be applied to the image processing method according to an exemplary embodiment. Accordingly, drawings and descriptions of the above-described image processing apparatus 100 may also be applied to the image processing method.

Figure 26:
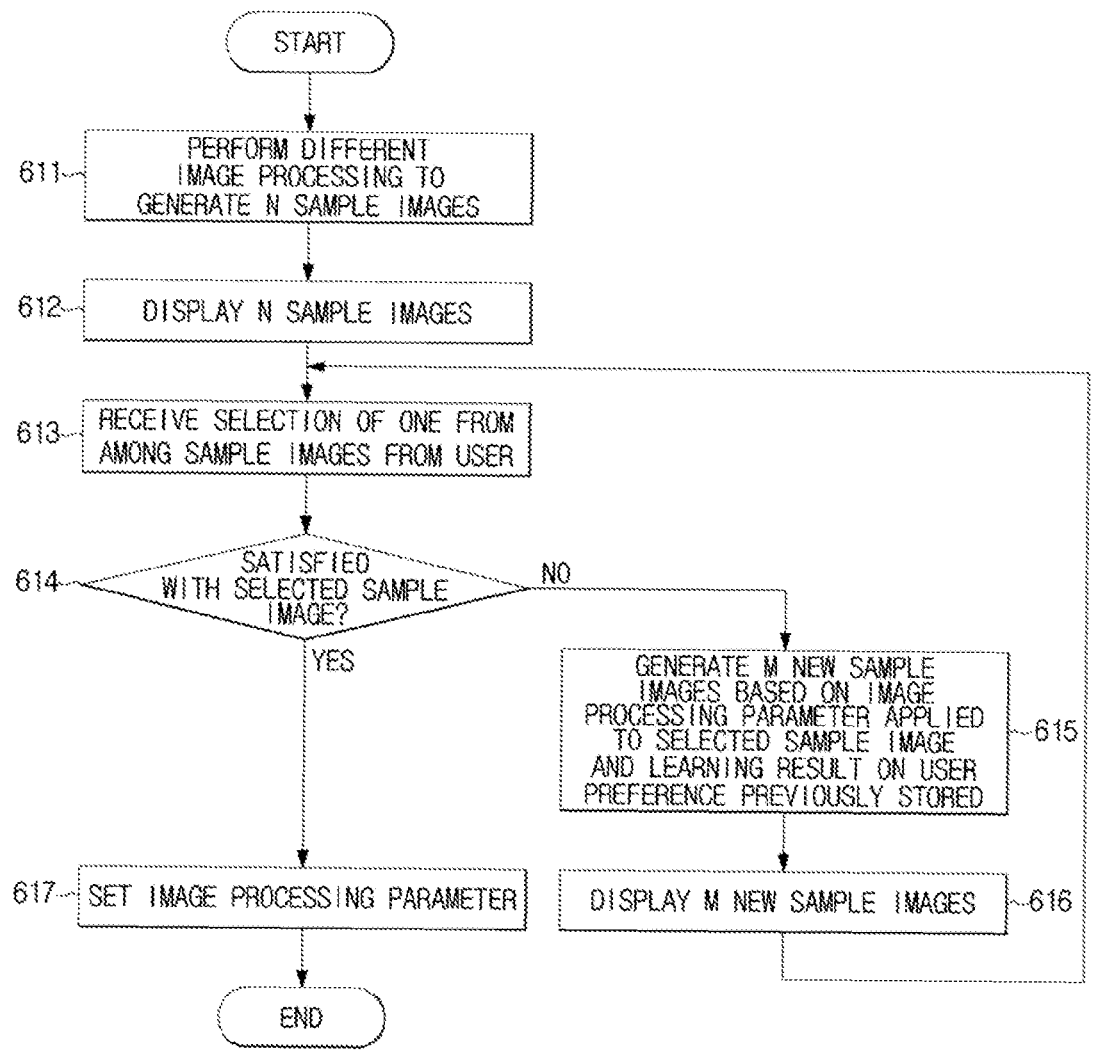
FIG. 26 is a flowchart illustrating an image processing method, according to an exemplary embodiment.

FIG. 26 is a flowchart illustrating an image processing method, according to an exemplary embodiment.

Referring to FIG. 26, in operations 611 and 612, different image processing operations are performed in order to generate and display N sample images (N is an integer equal to or greater than 2) on the display unit. However, the types or number N of sample images may not be limited. The types of the sample images may be determined according to or irrespective of the type of medical image processed by the image processing apparatus 100. In addition, the number of sample images may be set or changed by a user. Image processing may be performed on a plurality of sample images according to a parameter combination generally preferred by many users. All or only some of the image processing parameters may be set to different values. Whether the image processing parameters applied to the respective sample images are varied is not limited. However, a combination of the image processing parameters applied to one sample image may vary. The plurality of sample images may be displayed as shown in FIG. 13, 22, 23, or 24. However, these sample images are merely exemplary and may be displayed in other methods.

In operation 613, a selection of one from among the sample images is received from a user. The selection may be accomplished by touching or clicking a desired image from among displayed sample images according to the type of the input unit 142.

When the user is satisfied with the selected sample image (i.e., yes in operation 614), an image processing parameter is set based on the selected sample image in operation 617. An optimal image processing parameter combination preferred by a user may be output by inputting a combination of image processing parameters applied to the finally selected sample image to an algorithm or an artificial neural network formed by learning, and the image processing parameters may be set to the output image processing parameter combination. Alternatively, values of the image processing parameters applied to the finally selected sample image may be set without applying the learning.

When the user is not satisfied with the selected sample image (i.e., no in operation 614), new M sample images (M is an integer equal to or greater than 2) are generated (in operation 615) and displayed (in operation 616) based on image processing parameters applied to the selected sample image and a prestored learning result with respect to a user's preference. Here, M may be equal to or different from N. A process of receiving a selection of one of sample images from a user and setting an image processing parameter according to whether the user is satisfied with the selected image or generating and displaying a new sample image is repeated. In this aspect, an image processing parameter to be applied to new image processing may be determined based on learning of the parameter control unit 110 and the sample image selected by the user. For example, when the image processing parameters applied to the sample image selected in the previous step are input to an algorithm or an artificial neutral network formed by the learning of the parameter control unit 110, an optimized image processing parameter combination may be output appropriately based on a user's preference. The image processing unit 120 may perform image processing according to the output image processing parameter combination. As an example, if the sample image selected in the previous step is an image which has high contrast, the image processing unit 120 may minimize a variation in the contrast to keep the high contrast and change other image processing parameters in order to generate a plurality of new sample images.

Figure 27:
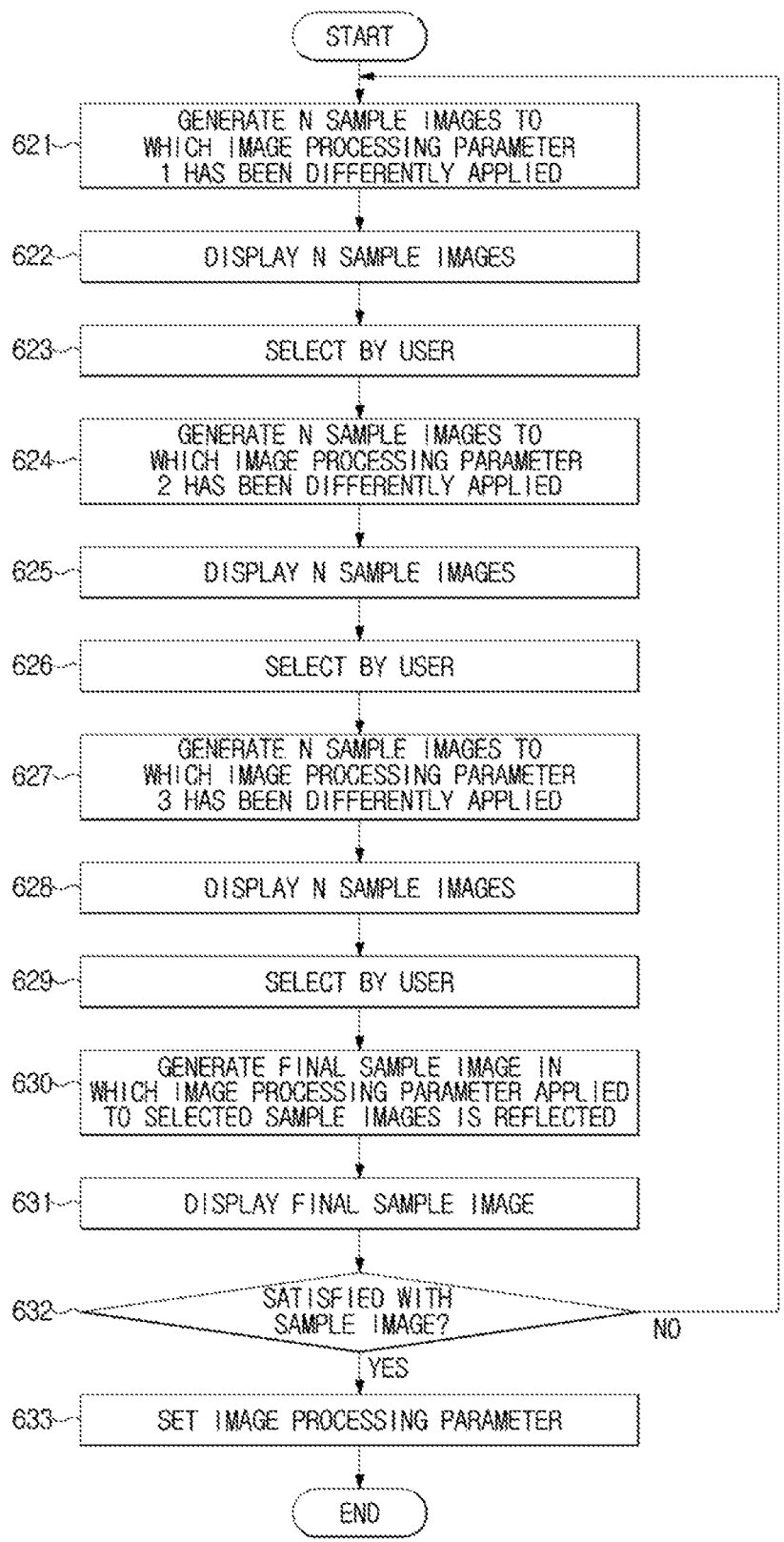
FIG. 27 is a flowchart illustrating another example of an image processing method, according to an exemplary embodiment.

FIG. 27 is a flowchart illustrating another example of an image processing method, according to an exemplary embodiment. In the example, a selection of three types of image processing parameters is received.

Referring to FIG. 27, N sample images to which image processing parameter 1 has been variably applied are generated (i.e., operation 621) and displayed (i.e., operation 622). Other than the image processing parameter 1, the same parameter values may be applied to the N sample images. In addition, a value optimized to the image processing parameter 1 may be applied to the N sample images. In addition, the image processing parameter 1 may also reflect a user's preference.

In operation 623, a selection of one of the displayed sample images is received from the user. Subsequently, N sample images to which image processing parameter 2 has been variably applied are generated (i.e., operation 624) and displayed (i.e., operation 625). The parameters having the same value, other than the image processing parameter 2, may be applied to the sample images. Alternatively, a value optimized to the image processing parameter 2 may be applied to the sample images. In addition, the image processing parameter 2 may also reflect the user's preference.

In operation 626, a selection of one of the displayed sample images is received from the user. Subsequently, N sample images to which image processing parameter 3 has been differently applied are generated (i.e., operation 627) and displayed (i.e., operation 628). The parameters having the same value, other than the image processing parameter 3, may be applied to the sample images. Alternatively, a value optimized to the image processing parameter 3 may be applied to the sample images. In addition, the image processing parameter 3 may also reflect the user's preference.

In operation 629, a selection of one of the displayed sample images is received from the user.

When all selections based on the sequential variations of image processing parameter 1, image processing parameter 2, and image processing parameter 3 are completed, a final sample image to which the image processing parameters applied to the selected sample images have been reflected is generated (i.e., operation 630) and displayed (i.e., operation 631). This is intended to prompt a confirmation of whether the user is satisfied (i.e., operation 632), and the image processing parameter 1 applied to the sample image selected in operation 623, the image processing parameter 2 applied to the sample image selected in operation 626, and the image processing parameter 3 applied to the sample image selected in operation 629 may be applied to a final sample image. Alternatively, the image processing parameters applied to the selected sample image may not be applied without change and may be further optimized based on learning of the parameter control unit 110.

When the user is satisfied with the final sample image (i.e., yes in operation 632), the image processing parameter applied to the final sample image is set without change in operation 633. When the user is not satisfied (i.e., no in operation 632), the sequential display and selection of the sample image in operations 621-631 are repeated again.

In an example of FIG. 27, the number of types of the image processing parameters is three. However, this is merely an example, and a smaller or larger number of types of image processing parameters may be set.

In the example of FIG. 27, a selection by the user in the previous step is not reflected in the sample image displayed in the current step. However, according to another example, the selection of the user in the previous step may be reflected in the sample image displayed in the current step. In particular, when the user selects one sample image from among sample images for the image processing parameter 1, the image processing parameter 1 applied to the sample image selected in the previous step may be applied to the sample image generated in the next step. In this case, even when the final sample image is not generated and displayed separately, a sample image selected in the last step may be the final sample image.

Figure 28:
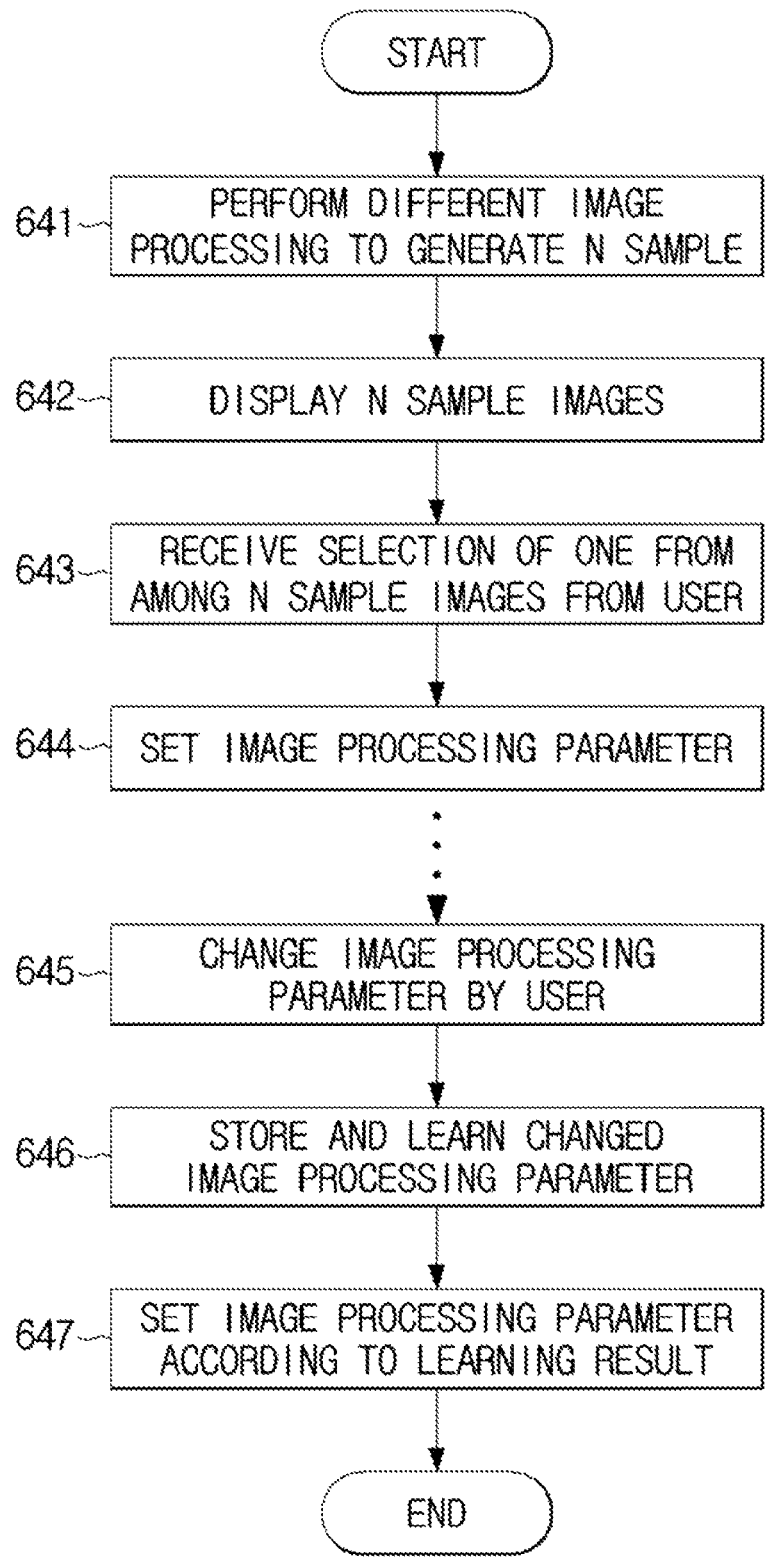
FIG. 28 is a flowchart illustrating still another example of an image processing method, according to an exemplary embodiment.

FIG. 28 is a flowchart illustrating still another example of an image processing method, according to an exemplary embodiment.

Referring to FIG. 28, image processing is variably performed in order to generate N sample images in operation 641, and the generated N sample images are displayed in operation 642. Here, the N sample images may be obtained by performing the image processing operations according to a parameter combination generally preferred by many users.

In operation 643, a selection of one from among N sample images is received from a user, and in operation 644, an image processing parameter is set based on the selected sample image. Parameters applied to the selected sample image may be set without change or may be optimized based on learning of the parameter control unit 110. In particular, the set image processing parameters are initial image processing parameters, and the setting of the initial image processing parameters may be accomplished upon first powering-up of the image processing apparatus 100 and/or periodically.

Even when the initial image processing parameters are set, the user may change the parameters while using the image processing apparatus 100 in operation 645, and the changed image processing parameters may be stored in the parameter DB and optimized based on the learning of the parameter control unit 110 in operation 646. In operation 647, the parameter control unit 110 sets an optimized parameter, that is, an image processing parameter according to a learning result. Accordingly, when a new image is displayed after the change of the parameters, the optimized image processing parameter may be applied. Accordingly, as the frequency of use increases, the image processing parameter may be gradually optimized appropriately to the user's preference.

The learning module of the parameter control unit 110 may include data stored in the parameter DB in the learning data, and may perform the learning whenever a new parameter is stored in the parameter DB. Accordingly, the learning result may be updated whenever the parameters are changed, and the learning data is accumulated as the frequency of use increases, thereby gradually optimizing the image processing parameters appropriately to the user's preference.

With the image processing apparatus, the medical imaging apparatus, and the image processing method according to an exemplary embodiment, it is possible to intuitively and easily set an image processing parameter which is usable for processing a medical image to a user-preferred optimal value.

Although a few exemplary embodiments have been shown and described, it will be appreciated by those of skill in the art that changes may be made in these exemplary embodiments without departing from the principles and spirit of the present inventive concept, the scope of which is defined in the claims and their equivalents.

What is claimed is:

1. An image processing apparatus, comprising:
a display configured to display a first plurality of sample images;
an input device configured to receive, from a user, a selection of at least one sample image from among the first plurality of sample images; and
a processor configured to generate a second plurality of sample images in which at least one image processing parameter from among a plurality of image processing parameters to be applied to the selected at least one sample image is changed, and to control the plurality of image processing parameters and to change the at least one image processing parameter to be applied to the selected at least one sample image based on machine learning that is implemented by using an algorithm that corresponds to an artificial neural network, wherein, when a parameter change request is received after the at least one image processing parameter is set, the processor is further configured to generate a plurality of new sample images to which the at least one image processing parameter has been variably applied based on an image processing parameter that is applied to the at least one sample image selected when the at least one image processing parameter is set.

2. The image processing apparatus of claim 1, wherein the processor is further configured to apply the changed at least one image processing parameter in order to generate the second plurality of sample images.

3. The image processing apparatus of claim 1, wherein,
the processor is further configured to repeatedly perform the generation of the second plurality of sample images, and
the display is further configured to repeatedly perform a display of the generated plurality of second sample images.

4. The image processing apparatus of claim 1, further comprising a storage configured to store preference data which relates to respective preferences of each of a plurality of users for the plurality of image processing parameters,
wherein the preference data includes a respective setting history of the plurality of image processing parameters for each of the plurality of users.

5. The image processing apparatus of claim 4, wherein the processor comprises:
a learning module configured to perform machine learning with respect to the preference data; and
a determination module generated by the learning module.

6. The image processing apparatus of claim 1, wherein the processor is further configured to set the at least one image processing parameter based on the at least one sample image selected by the user.

7. The image processing apparatus of claim 6, wherein the processor is further configured to change the at least one image processing parameter to be applied to the selected at least one sample image and to store the changed at least one image processing parameter.

8. The image processing apparatus of claim 1, wherein the processor is further configured to perform at least one image processing operation with respect to a medical image acquired by a medical imaging apparatus connected with the image processing apparatus in order to generate the second plurality of sample images.

9. The image processing apparatus of claim 1, wherein the processor is further configured to perform at least one image processing operation with respect to a medical image stored in a storage in order to generate the second plurality of sample images.

10. The image processing apparatus of claim 1, wherein the processor is further configured to set the at least one image processing parameter for each part shown in a medical image with respect to which image processing is to be performed.

11. The image processing apparatus of claim 1, wherein the processor is further configured to set the at least one image processing parameter for each user from among a plurality of users.

12. An image processing apparatus, comprising:
a display configured to display a first plurality of sample images to which a first image processing parameter from among a plurality of image processing parameters has been variably applied to a second plurality of sample images to which an nth image processing parameter from among the plurality of image processing parameters has been variably applied, wherein n is an integer that is greater than or equal to two;
an input device configured to receive, from a user, a selection of one sample image from among the displayed first plurality of sample images; and
a processor configured to set the first image processing parameter based on the nth image processing parameter applied to the selected sample image and to optimize the plurality of image processing parameters to be applied to the selected sample image based on machine learning that is implemented by using an algorithm that corresponds to an artificial neural network,
wherein, when a parameter change request is received after the first image processing parameter is set, the processor is further configured to generate a plurality of new sample images to which the first image processing parameter has been variably applied based on an image processing parameter that is applied to the one sample image selected when the first image processing parameter is set.

13. The image processing apparatus of claim 12, wherein the processor is further configured to store the plurality of image processing parameters that are applied to the selected sample image.

14. The image processing apparatus of claim 12, wherein the processor is further configured to store the optimized plurality of image processing parameters.

15. An image processing apparatus, comprising:
a display configured to display a first plurality of sample images to which at least a first image processing parameter from among a plurality of image processing parameters has been variably applied;
an input device configured to receive, from a user, a selection of one sample image from among the displayed first plurality of sample images; and
a processor configured to set the at least first image processing parameter based on a second image processing parameter from among the plurality of image processing parameters that is applied to the selected sample image, and when the at least first image processing parameter is changed, to apply machine learning that is implemented by using an algorithm that corresponds to an artificial neural network to the changed at least first image processing parameter in order to determine a new image processing parameter from among the plurality of image processing parameters,
wherein, when a parameter change request is received after the at least first image processing parameter is set, the processor is further configured to generate a plurality of new sample images to which the at least first image processing parameter has been variably applied based on an image processing parameter that is applied to the one sample image selected when the at least first image processing parameter is set.

16. The image processing apparatus of claim 15, wherein the processor is further configured to perform a setting of the at least first image processing parameter upon an initial execution performed by the image processing apparatus or periodically.

17. The image processing apparatus of claim 16, wherein the processor is further configured to include the changed at least first image processing parameter in learning data which is used for the application of the machine learning.

18. A medical imaging apparatus comprising:
a scanner configured to scan a target object in order to acquire a medical image; and
an image processing apparatus configured to set at least a first image processing parameter from among a plurality of image processing parameters to be applied to the medical image,
wherein the image processing apparatus includes:
a display configured to display a first plurality of sample images to which the at least first image processing parameter has been variably applied;
an input device configured to receive, from a user, a selection of at least one sample image from among the displayed first plurality of sample images;
a processor configured to generate a second plurality of sample images for which the at least first image processing parameter applied to the selected sample image is changed, and to control the plurality of image processing parameters and to change the at least one image processing parameter to be applied to the selected at least one sample image based on machine learning that is implemented by using an algorithm that corresponds to an artificial neural network,
wherein, when a parameter change request is received after the at least one image processing parameter is set, the processor is further configured to generate a plurality of new sample images to which the at least one image processing parameter has been variably applied based on an image processing parameter that is applied to the at least one sample image selected when the at least one image processing parameter is set.

19. The medical imaging apparatus of claim 18, wherein the processor is further configured to apply the changed at least first image processing parameter in order to generate the second plurality of sample images.

20. The medical imaging apparatus of claim 18, wherein, the processor is further configured to repeatedly perform the generation of the second plurality of sample images, and
the display is further configured to repeatedly perform a display of the generated second plurality of sample images.

21. An image processing method, comprising:
displaying a first plurality of sample images;
receiving, from a user, a selection of one sample image from among the displayed first plurality of sample images; and
generating a second plurality of sample images in which at least one image processing parameter from among a plurality of image processing parameters to be applied to the selected sample image is changed; and
controlling the plurality of image processing parameters and changing the at least one image processing parameter to be applied to the selected sample image based on machine learning that is implemented by using an algorithm that corresponds to an artificial neural network,
wherein, when a parameter change request is received after the at least one image processing parameter is changed, the processor is further configured to generate a plurality of new sample images to which the at least one image processing parameter has been variably applied based on an image processing parameter that is applied to the one sample image selected when the at least one image processing parameter is changed.

22. The image processing method of claim 21, further comprising setting the at least one image processing parameter based on the selected sample image.

23. The image processing method of claim 22, wherein the setting the at least one image processing parameter comprises changing the at least one image processing parameter to be applied to the selected sample image and storing the changed at least one image processing parameter.

24. An image processing method, comprising:
obtaining a first image generated by a medical imaging apparatus;
using the obtained first image to generate a first plurality of sample images by varying a first image processing parameter from among a plurality of image processing parameters with respect to the obtained first image;
receiving, from a user, a first selection of an image from among the generated first plurality of sample images;
setting the first image processing parameter based on the first user-selected image and based on machine learning that is implemented by using an algorithm that corresponds to an artificial neural network;
using the first user-selected image to generate a second plurality of sample images by varying a second image processing parameter from among the plurality of image processing parameters with respect to the first user-selected image;
receiving, from the user, a second selection of an image from among the generated second plurality of sample images; and
setting the second image processing parameter based on the second user-selected image and based on the machine learning that is implemented by using the algorithm that corresponds to the artificial neural network,
wherein using the obtained first image to generate the first plurality of sample images comprises controlling all of the plurality of image processing parameters other than the first image processing parameter to be constant, and
wherein the using the first user-selected image to generate the second plurality of sample images comprises controlling all of the plurality of image processing parameters other than the second first image processing parameter to be constant.

25. The image processing method of claim 24, further comprising:
using the second user-selected image to generate a third plurality of sample images by varying a third image processing parameter with respect to the second user-selected image;
receiving, from the user, a third selection of an image from among the generated third plurality of sample images; and
setting the third image processing parameter based on the third user-selected image.

26. The image processing method of claim 24, wherein each of the first image processing parameter and the second image processing parameter includes at least one from among a noise parameter, a sharpness parameter, and a contrast parameter.

27. The image processing method of claim 24, wherein the medical imaging apparatus includes at least one from among a medical ultrasound imaging apparatus, an X-ray radiography apparatus, a magnetic resonance imaging (MRI) apparatus, a mammography apparatus, a positron emission tomography (PET) apparatus, a computed tomography (CT) apparatus, a single photon emission computed tomography (SPECT) apparatus, and an optical coherence tomography (OCT) apparatus.

* * * * *